United States Patent
Lu et al.

(10) Patent No.: US 7,566,454 B2
(45) Date of Patent: Jul. 28, 2009

(54) INFLUENZA NUCLEIC ACIDS, POLYPEPTIDES, AND USES THEREOF

(75) Inventors: Shan Lu, Franklin, MA (US); Shixia Wang, Northborough, MA (US)

(73) Assignee: University of Massachusetts, Boston, MA (US)

( * ) Notice: Subject to any disclaimer, the term of this patent is extended or adjusted under 35 U.S.C. 154(b) by 127 days.

(21) Appl. No.: 11/362,617

(22) Filed: Feb. 24, 2006

(65) Prior Publication Data

US 2006/0217338 A1    Sep. 28, 2006

Related U.S. Application Data

(60) Provisional application No. 60/655,979, filed on Feb. 24, 2005.

(51) Int. Cl.
| | |
|---|---|
| A61K 39/12 | (2006.01) |
| A61K 39/145 | (2006.01) |
| A61K 31/00 | (2006.01) |
| A61K 38/00 | (2006.01) |
| A61K 31/70 | (2006.01) |

(52) U.S. Cl. ............. 424/184.1; 424/204.1; 424/209.1; 424/210.1; 514/1; 514/2; 514/44; 514/888

(58) Field of Classification Search .................. None
See application file for complete search history.

(56) References Cited

U.S. PATENT DOCUMENTS

2002/0045594 A1*  4/2002  Volkin et al. .................. 514/44

2006/0024670 A1*  2/2006  Luke et al. ..................... 435/5

FOREIGN PATENT DOCUMENTS

WO    WO 03/075955    9/2003

OTHER PUBLICATIONS

Davis, et al. Expression of antigenic determinants of the hemagglutinin gene of a human influenza virus in *Escherichia coli*. Proc. Nat. Acad. Sci. USA 1981; vol. 78, No. 9, pp. 5376-5380.*
Wang, et al. DNA replicative functions of highly-expressed, codon-optimized human papillomavirus proteins E1 and E2. J Virol Meth. 2003; 108:83-90.*
Montgomery, et al. Heterologous and homologous protection against influenza A by DNA vaccination: optimization of DNA vectors. DNA Cell. Biol. 1993; 12:777-783. Abstract Only.*
Ramsay, et al. DNA vaccination against virus infection and enhancement of antiviral immunity following consecutive immunization with DNA and viral vectors. Immunology and Cell Biology (1997) 75: 382-388.*
Shedlock and Weiner. DNA vaccination: antigen presentation and the induction of immunity. Journal of Leukocyte Biology. 2000;68(6): 793-806.*

(Continued)

*Primary Examiner*—Bruce Campell
*Assistant Examiner*—Stuart W Snyder
(74) *Attorney, Agent, or Firm*—Fish & Richardson P.C.

(57) ABSTRACT

Codon-optimized nucleic acids encoding influenza polypeptides and uses of the nucleic acids and polypeptides for inducing immune responses are provided herein.

18 Claims, 21 Drawing Sheets

H1 HA codon optimized polypeptides

OTHER PUBLICATIONS

Bright et al., "Impact of glycosylation on the immunogenicity of a DNA-based influenza H5 HA vaccine," *Virology*, vol. 308:270-278 (2003).
Fynan et al., "DNA vaccines: Protective immunizations by parenteral, mucosal, and gene-gun inoculations," *Proc. Natl. Acad. Sci. USA*, vol. 90:11478-11482 (1993).
Justewicz et al., "Antibody-Forming Cell Response to Virus Challenge in Mice Immunized with DNA Encoding the Influenza Virus Hemagglutinin," *Journal of Virology*, vol. 69:7712-7717 (1995).
Kodihalli et al., "Strategies for inducing protection against avian influenza A virus subtypes with DNA vaccines," *Vaccine*, vol. 18:2592-2599 (2000).
Oran et al., "DNA Vaccines: Influenza Virus Challenge of a Th2/Tc2 Immune Response Results in a Th2/Tc1 Response in the Lung," *Journal of Virology*, vol. 78:4376-4380 (2004).
Plotkin et al., "Codon bias and frequency-dependent selection on the hemagglutinin epitopes of influenza A virus," *Proc. Natl. Acad. Sci. USA*, vol. 100:7152-7157 (2003).
Sasaki et al., "Regulation of DNA-Raised Immune Responses by Cotransfected Interferon Regulatory Factors," *Journal of Virology*, vol. 76:6652-6659 (2002).
Sasaki et al., "Improvement of DNA vaccine immunogenicity by a dual antigen expression system," *Biochem Biphys Res Commun.*, vol. 315:38-43 (2004).
Yang et al., "Codon-Substitution Models for Heterogeneous Selection Pressure at Amino Acid Sites," *Genetics*, vol. 155:431-449 (2000).
Belshe et al., "Serum Antibody Responses after Intradermal Vaccination against Influenza," *The New England Journal of Medicine*, vol. 351:2286-2294 (2004).
Couch, "Influenza: Prospects for Control," *Ann. Intern. Med.*, vol. 133:992-998 (2000).
Fan et al., "Preclinical study of influenza virus A M2 peptide conjugate vaccines in mice, ferrets, and rhesus monkeys," *Vaccine*, vol. 22:2293-3003 (2004).
Fynan et al., "Use of DNA Encoding Influenza Hemagglutinin as an Avian Influenza Vaccine," *DNA Cell Biology*, vol. 12:785-789 (1993).
Hoffmann et al., "Eight-plasmid system for rapid generation of influenza virus vaccines," *Vaccine*, vol. 20:3165-3170 (2002).
Katz et al., "Preparing for the Next Influenza Pandemic," *ASM News*, vol. 70(9):412-419 (2004).
Kenney et al., "Dose Sparing with Intradermal Injection of Influenza Vaccine," *The New England Journal of Medicine*, vol. 351:2295-2301 (2004).
Lamb et al., "Influenza Virus $M_2$ Protein Is an Integral Membrane Protein Expressed on the Infected-Cell Surface," *Cell.*, vol. 40:627-633 (1985).
Lu et al., "Antigen Engineering in DNA Immunization," *Methods in Molecular Medicine*, vol. 29:355-374 (1998).
Mirzabekov et al., "Enhanced Expression, Native Purification, and Characterization of CCR5, a Principal HIV-1 Coreceptor," *The Journal of Biological Chemistry*, vol. 274:28745-28750 (1999).
Neirynck et al., "A universal influenza A vaccine based on the extracellular domain of the M2 protein," *Nature Medicine*, vol. 5:1157-1163 (1999).
Palese et al., "Influenza vaccines: present and future," *The Journal of Clinical Investigation*, vol. 110:9-13 (2002).
Peiris et al., "Human infection with influenza H9N2," *The Lancet*, vol. 354:916-917 (1999).
Shaw et al., "New Aspects of Influenza Viruses," *Clinical Microbiology Reviews*, vol. 5:74-92 (1992).
Skehel et al., "Receptor Binding and Membrane Fusion in Virus Entry: The Influenza hemagglutinin," *Annu. Rev. Biochem.*, vol. 69:531-569 (2000).
Ulmer et al., "Heterologous Protection Against Influenza by Injection of DNA Encoding a Viral Protein," *Science*, vol. 259:1745-1749 (1993).
Wang et al., "Ion Channel Activity of Influenza A Virus $M_2$ Protein: Characterization of the Amantadine Block," *Journal of Virology*, vol. 67:5585-5594 (1993).
Wang et al., "Delivery of DNA to skin by particle bombardment," *Methods in Molecular Biology*, vol. 245:185-196 (2004).
Wang et al., "Identification of Two Neutralizing Regions on the Severe Acute Respiratory Syndrome Coronavirus Spike Glycoprotein Produced from the Mammalian Expression System," *Journal of Virology*, vol. 79:1906-1910 (2005).
Webby et al., "Are we ready for pandemic influenza?," *Science*, vol. 302:1519-1522 (2003).
Wright et al., "Orthomyxoviruses," Fields Virology, $4^{th}$ Ed., Knipe and Howley, Eds., Lippincott, Williams & Wilkins, vol. 1:1533-1579 (2001).
GenBank Accession No. AJ344014, 2 pages (2002).
GenBank Accession No. AJ457937, 2 pages (2001).
Chen, *Chinese Medical Journal*, vol. 117, pp. 125-132 (2004).
Chen, et al., *Vaccine*, vol. 17, pp. 653-659 (1999).
Couch, et al., *Journal of Infectious Diseases*, vol. 176, pp. S38-S44 (1997).
Degano, et al., *Vaccine*, vol. 18, pp. 623-632 (2000).
Fiers, et al., *Virus Research*, vol. 103, pp. 173-176 (2004).
Frelin, et al., *Gene Therapy*, vol. 11, pp. 522-533 (2004).
Marwick, *JAMA*, vol. 279, pp. 1150-1151 (1998).
Smith, et al., *MMWR: Recommendations and Reports*, vol. 55, pp. 1-63 (2006).
2006-07 Influenza Vaccine Composition, Centers for Disease Control, retrieved from the World Wide Web at cdc.gov/flu/professionals/vaccination/composition0607.htm (2006).
Database EMBL accession No. Q6WG00, "Hemagglutinin" Jul. 5, 2004.
Database EMBL accession No. Q6XTN3, "Neuraminidase" Jul. 5, 2004.
Liu, et al. "Polynucleotide viral vaccines: codon optimization and ubiquitin conjugation enhances prophylactic and therapeutic efficacy" Vaccine 20(5-6):862-869 (2001).

* cited by examiner

FIG 1A. Codon optimized influenza A H1 HA nucleic acid sequence:

ATGAAGGCCAAGCTGCTGGCCCTGCTGTGCACCTTCACCGCCACCTACGCCGACACCATCTGCAT
CGGCTACCACGCCAACAACAGCACCGACACCGTGGATACCGTGCTGGAGAAGAACGTGACAGTGA
CCCACAGCGTGAACCTGCTGGAGGACAGCCACAACGGCAAGCTGTGTCTGCTGAAAGGCATCGCC
CCCCTGCAGCTGGGCAACTGTAGCGTGGCCGGCTGGATTCTGGGCAACCCCGAATGCGAGCTGCT
GATCTCCAAGGAGAGCTGGAGCTACATCGTGGAGACCCCCAACCCCGAGAATGGCACCTGCTACC
CCGGCTACTTCGCCGACTACGAGGAGCTGCGGGAGCAGCTGAGCAGCGTGAGCAGCTTCGAGAGA
TTCGAGATCTTCCCCAAGGAAAGCAGCTGGCCCAACCACACCGTGACCGGAGTGAGCGCCAGCTG
CAGCCACAATGGGAAGAGCAGCTTCTACAGAAATCTGCTGTGGCTGACCGGCAAGAACGGCCTGT
ACCCCAACCTGAGCAAGTCCTACGTGAACAACAAAGAGAAGGAAGTGCTGGTGCTGTGGGGCGTG
CACCACCCCCCTAACATCGGCAACCAGCGGGCCCTGTACCACACCGAGAACGCCTATGTGAGCGT
GGTGAGCAGCCACTACAGCAGAAGATTCACCCCCGAGATCGCCAAGAGACCCAAAGTGAGAGATC
AGGAGGGCAGAATCAACTACTACTGGACCCTGCTGGAGCCCGGCGACGCCATCATCTTCGAGGCC
AACGGCAACCTGATCGCCCCCTGGTACGCCTTCGCCCTGAGCAGAGGCTTCGGCAGCGGCATCAT
CACCAGCAATGCCCCCATGGACGAATGCGACGCCAAGTGTCAGACACCCCAGGGCGCCATCAACA
GCAGCCTGCCCTTCCAGAACGTGCACCCCGTGACCATCGGAGAGTGCCCCAAGTACGTGCGGAGC
GCCAAGCTGCGGATGGTGACCGGCCTGCGGAACATCCCCAGCATTCAGAGCAGAGGCCTGTTCGG
CGCCATCGCCGGCTTCATCGAGGGCGGCTGGACCGGCATGGTGGACGGCTGGTATGGCTACCAC
ACCAGAACGAGCAGGGATCTGGCTACGCCGCCGATCAGAAGAGCACCCAGAACGCCATCAACGGC
ATCACCAACAAAGTGAACAGCGTGATCGAGAAGATGAACACCCAGTTCACAGCCGTGGGCAAGGA
GTTCAACAAACTGGAGCGGCGGATGGAAACCCTGAACAAGAAAGTGGACGACGGCTTCCTGGACA
TCTGGACCTACAACGCCGAGCTGCTGGTGCTGCTGGAGAATGAGCGGACCCTGGACTTCCACGAC
AGCAACGTGAAGAACCTGTACGAGAAAGTGAAGAGCCAGCTGAAGAACAACGCCAAGGAGATCGG
CAACGGCTGCTTCGAGTTCTACCACAAGTGCAACAACGAGTGCATGGAGAGCGTGAAGAACGGCA
CCTACGACTACCCCAAGTACTCCGAGGAGAGCAAGCTGAACCGGGAGAAGATCGACGGCGTGAAG
CTGGAGAGCATGGGCGTGTACCAGATCCTGGCCATCTACAGCACCGTGGCCAGCAGCCTGGTGCT
GCTGGTGAGCCTGGGCGCCATCTCTTTCTGGATGTGCTCCAACGGCAGCCTGCAGTGCAGAATCT
GCATCTGA (SEQ ID NO:1)

FIG 1B. Influenza A H1 HA amino acid sequence:

MKAKLLALLCTFTATYADTICIGYHANNSTDTVDTVLEKNVTVTHSVNLLEDSHNGKLCLLKGIA
PLQLGNCSVAGWILGNPECELLISKESWSYIVETPNPENGTCYPGYFADYEELREQLSSVSSFER
FEIFPKESSWPNHTVTGVSASCSHNGKSSFYRNLLWLTGKNGLYPNLSKSYVNNKEKEVLVLWGV
HHPPNIGNQRALYHTENAYVSVVSSHYSRRFTPEIAKRPKVRDQEGRINYYWTLLEPGDAIIFEA
NGNLIAPWYAFALSRGFGSGIITSNAPMDECDAKCQTPQGAINSSLPFQNVHPVTIGECPKYVRS
AKLRMVTGLRNIPSIQSRGLFGAIAGFIEGGWTGMVDGWYGYHHQNEQGSGYAADQKSTQNAING
ITNKVNSVIEKMNTQFTAVGKEFNKLERRMETLNKKVDDGFLDIWTYNAELLVLLENERTLDFHD
SNVKNLYEKVKSQLKNNAKEIGNGCFEFYHKCNNECMESVKNGTYDYPKYSEESKLNREKIDGVK
LESMGVYQILAIYSTVASSLVLLVSLGAISFWMCSNGSLQCRICI (SEQ ID NO:2)

FIG. 2A. Codon optimized influenza A H3 HA nucleic acid sequence:

ATGAAAACCATCATCGCCCTGAGCTACATCCTGTGCCTGGTGTTCGCCCAGAAACTGCCCGGCAA
CGACAACAGCACCGCCACCCTGTGTCTGGGCCACCACGCCGTGAGCAACGGCACCCTGGTGAAAA
CCATCACCAATGACCAGATCGAAGTGACCAACGCCACCGAGCTGGTGCAGAGCAGCAGCACCGGC
AGAATCTGCGACAGCCCTCACCAGATCCTGGACGGCGAGAACTGTACCCTGATCGACGCCCTGCT
GGGAGACCCTCACTGCGACGGCTTCCAGAACAAGGAGTGGGACCTGTTCGTGGAGCGCAGCAAGG
CCTACAGCAACTGCTACCCTTACGACGTGCCCGACTACGCCTCCCTGCGGAGCCTGGTGGCCAGC
TCTGGCACCCTGGAGTTCAACAACGAGAGCTTCAATTGGACCGGCGTGGCCCAGAACGGCACCAG
CAGCGCCTGCAAGCGGAGAAGCAACAAGAGCTTCTTCAGCAGACTGAACTGGCTGCACCAGCTGA
AGTACAAGTACCCCGCCCTGAACGTGACCATGCCCAACAACGAAAAGTTCGACAAACTGTACATT
TGGGGCGTGCACCACCCCAGCACCGACAGCGACCAGATCAGCATCTACGCCCAGGCCAGCGGCAG
AGTGACCGTGTCTACCAAGAGAAGCCAGCAGACCGTGATCCCCAATATCGGCAGCAGACCCTGGG
TGCGGGGCGTGTCCAGCGGAATCTCCATCTACTGGACAATCGTGAAGCCCGGCGACATCCTGCTG
ATCAACTCCACCGGCAACCTGATTGCCCCTCGGGGCTACTTCAAGATCCGGAGCGGCAAAAGCAG
CATCATGCGGAGCGATGCCCCCATCGGCAAGTGCAACAGCGAGTGCATCACCCCCAACGGCAGCA
TCCCCAATGACAAGCCCTTCCAGAACGTGAACCGGATCACCTACGGCGCCTGCCCCAGATACGTG
AAGCAGAACACCCTGAAGCTGGCCACAGGAATGCGGAACGTGCCCGAGAAGCAGACCCGGGGCAT
CTTCGGCGCCATCGCCGGCTTCATCGAGAATGGCTGGGAGGGCATGGTGGACGGCTGGTACGGCT
TCCGGCACCAGAACAGCGAGGGCACCGGACAGGCCGACCTGAAGAGCACCCAGGCCGCCATCAAC
CAGATCAACGGCAAGCTGAACCGGCTGATCGAGAAAACCAACGAGAAGTTCCACCAGATCGAGAA
GGAGTTCAGCGAAGTGGAAGGCAGAATCCAGGACCTGGAGAAGTACGTGGAGGACACCAAGATCG
ATCTGTGGAGCTACAACGCCGAGCTGCTGGTCGCCCTGGAGAACCAGCACACCATCGACCTGACC
GACTCCGAGATGAACAAACTGTTCGAGAGAACCAAGAAGCAGCTGCGGGAGAACGCCGAGGACAT
GGGCAACGGCTGTTTCAAGATCTACCACAAGTGCGACAACGCCTGCATCGGCAGCATCAGAAACG
GCACCTACGACCACGACGTGTACAGAGATGAGGCCCTGAACAACCGGTTCCAGATCAAGGGCGTG
GAGCTGAAGAGCGGCTACAAGGATTGGATTCTGTGGATCTCCTTCGCCATCAGCTGCTTCCTGCT
GTGCGTGGTGCTGCTGGGCTTCATCATGTGGGCCTGTCAGAAGGGCAACATCCGGTGCAACATCT
GCATCTGA (SEQ ID NO:3)

FIG. 2B. Influenza A H3 HA amino acid sequence:

MKTIIALSYILCLVFAQKLPGNDNSTATLCLGHHAVSNGTLVKTITNDQIEVTNATELVQSSSTG
RICDSPHQILDGENCTLIDALLGDPHCDGFQNKEWDLFVERSKAYSNCYPYDVPDYASLRSLVAS
SGTLEFNNESFNWTGVAQNGTSSACKRRSNKSFFSRLNWLHQLKYKYPALNVTMPNNEKFDKLYI
WGVHHPSTDSDQISIYAQASGRVTVSTKRSQQTVIPNIGSRPWVRGVSSGISIYWTIVKPGDILL
INSTGNLIAPRGYFKIRSGKSSIMRSDAPIGKCNSECITPNGSIPNDKPFQNVNRITYGACPRYV
KQNTLKLATGMRNVPEKQTRGIFGAIAGFIENGWEGMVDGWYGFRHQNSEGTGQADLKSTQAAIN
QINGKLNRLIEKTNEKFHQIEKEFSEVEGRIQDLEKYVEDTKIDLWSYNAELLVALENQHTIDLT
DSEMNKLFERTKKQLRENAEDMGNGCFKIYHKCDNACIGSIRNGTYDHDVYRDEALNNRFQIKGV
ELKSGYKDWILWISFAISCFLLCVVLLGFIMWACQKGNIRCNICI (SEQ ID NO:4)

FIG. 3A. H1 HA codon optimized polypeptides
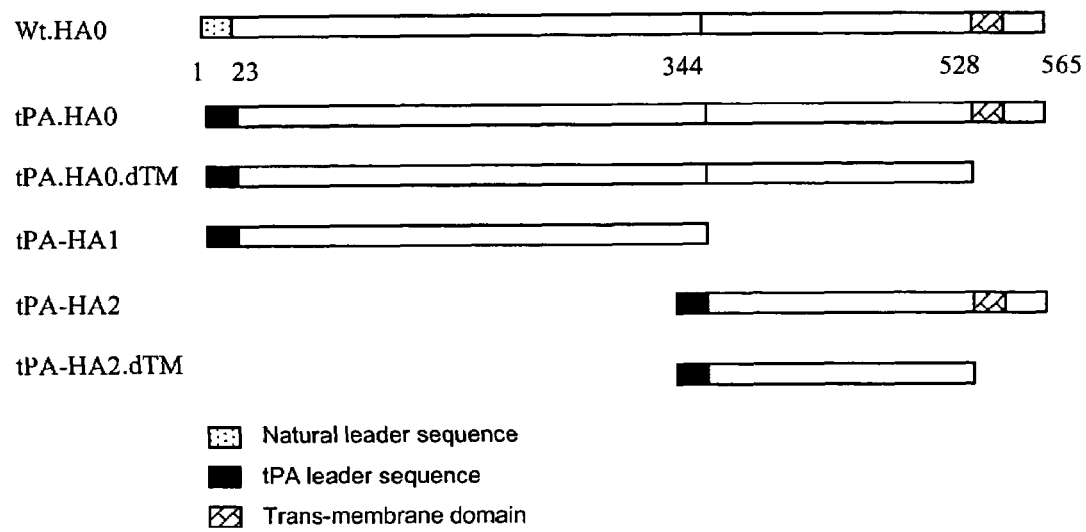
FIG. 3B. H3 HA codon optimized polypeptides
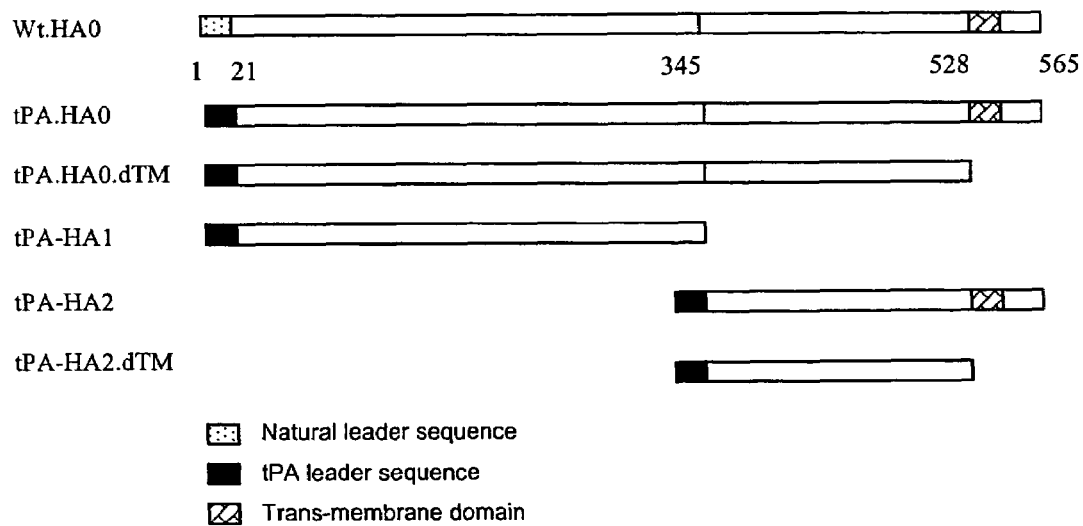

A. H1 HA expression:
1. Wt.HA0
2. Vector

B. H1 HA expression:
1. Wt.HA0
2. Vector

Antibody responses to H1 HA antigen

FIG. 6A Codon optimized influenza A N2 NA nucleic acid sequence:

ATGAACCCCAACCAGAAGATCATCACCATCGGCAGCGTGAGCCTCACCATCGCCACCGT
GTGCTTCCTCATGCAGATTGCCATCCTGGTGACCACCGTGACACTGCACTTCAAGCAGT
ACGAGTGCGACTCCCCCGCCAGCAACCAGGTGATGCCCTGCGAGCCCATCATCATCGAG
CGGAACATCACCGAGATCGTGTACCTGAACAACACCACCATCGAGAAAGAGATCTGCCC
CAAGGTAGTGGAGTACCGGAACTGGAGCAAGCCCAGTGCCAGATCACCGGCTTTGCCC
CCTTCAGCAAGGACAACAGCATCCGGCTGAGCGCTGGCGGCGACATCTGGGTGACCAGA
GAACCCTATGTGAGCTGCGACCACGGCAAGTGCTACCAGTTCGCCCTCGGCCAGGGCAC
CACACTGGACAACAAGCACAGCAATGACACCATCCACGACAGAATCCCTCACCGAACCC
TGCTGATGAACGAGCTGGGCGTGCCCTTCCACCTGGGCACACGGCAAGTGTGCATCGCC
TGGTCCAGCAGCAGCTGCCACGATGGCAAAGCCTGGCTGCACGTGTGCATCACAGGCGA
CGACAAGAATGCCACCGCCAGCTTCATCTACGACGGCCGGCTGGTGGACAGCATTGGCA
GCTGGAGCCAGAACATCCTCCGGACCCAGGAGAGCGAGTGCGTGTGCATCAATGGCACC
TGCACCGTGGTGATGACCGACGGCAGCGCCAGCGGCAGAGCCGACACAAGAATCCTGTT
CATCGAGGAGGGCAAGATCGTCCACATCAGCCCCCTGAGCGGCAGCGCCCAGCACGTGG
AAGAGTGCTCCTGCTATCCCCGGTACCCTGGCGTCCGGTGCATCTGTAGAGACAACTGG
AAGGGCAGCAACCGGCCCGTGGTGGACATCAACATGGAGGACTACAGCATCGACTCCAG
CTACGTGTGCAGCGGCCTGGTGGGCGACACACCCCGGAACGACGACCGGAGCAGCAACA
GCAACTGCCGGAACCCCAACAATGAGAGAGGCAACCAAGGAGTGAAGGGCTGGGCCTTC
GACAATGGCGATGACGTGTGGATGGGCCGGACCATCAGCAAGGACCTGCGCAGCGGCTA
CGAGACCTTCAAGGTGATTGGCGGCTGGTCCACCCCCAACTCCAAGAGCCAGATCAACA
GACAGGTGATCGTGGACAGCGACAACCGGAGCGGCTACAGCGGCATCTTCAGCGTGGAG
GGCAAGAGCTGCATCAACCGGTGCTTCTACGTGGAGCTGATCCGGGGCCGGAAGCAGGA
GACCAGAGTGTGGTGGACCAGCAACAGCATCGTGGTGTTCTGTGGCACCAGCGGCACCT
ACGGCACCGGCAGCTGGCCTGATGGCGCCAACATCAACTTCATGCCCATCTAA (SEQ
ID NO:5)

FIG. 6B Influenza A N2 NA amino acid sequence:

MNPNQKIITIGSVSLTIATVCFLMQIAILVTTVTLHFKQYECDSPASNQVMPCEPIIIE
RNITEIVYLNNTTIEKEICPKVVEYRNWSKPQCQITGFAPFSKDNSIRLSAGGDIWVTR
EPYVSCDHGKCYQFALGQGTTLDNKHSNDTIHDRIPHRTLLMNELGVPFHLGTRQVCIA
WSSSSCHDGKAWLHVCITGDDKNATASFIYDGRLVDSIGSWSQNILRTQESECVCINGT
CTVVMTDGSASGRADTRILFIEEGKIVHISPLSGSAQHVEECSCYPRYPGVRCICRDNW
KGSNRPVVDINMEDYSIDSSYVCSGLVGDTPRNDDRSSNSNCRNPNNERGNQGVKGWAF
DNGDDVWMGRTISKDLRSGYETFKVIGGWSTPNSKSQINRQVIVDSDNRSGYSGIFSVE
GKSCINRCFYVELIRGRKQETRVWWTSNSIVVFCGTSGTYGTGSWPDGANINFMPI
(SEQ ID NO:6)

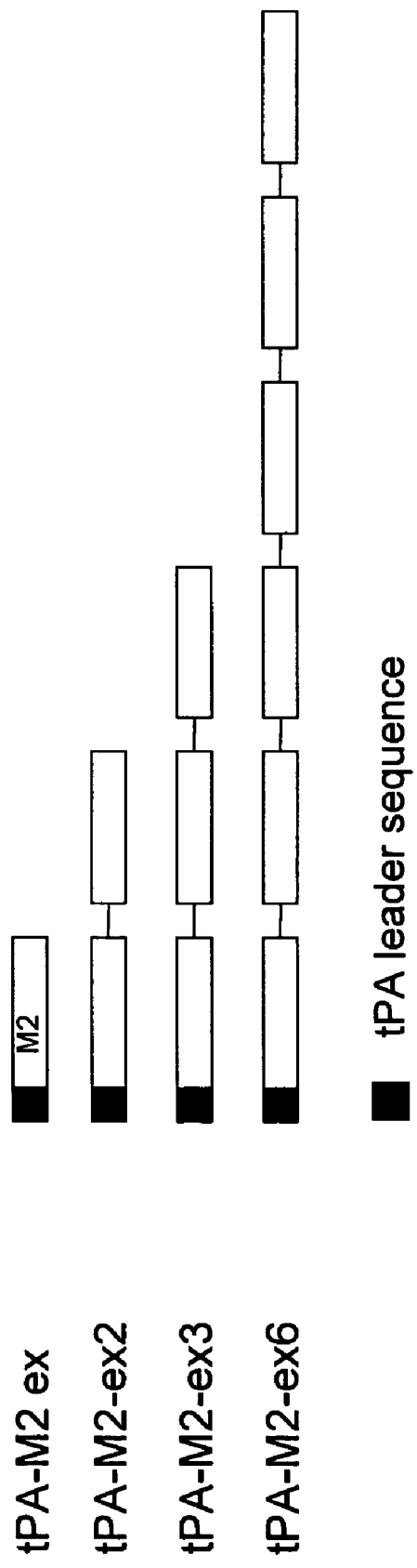
FIG. 7. Influenza ion-channel M2 DNA constructs

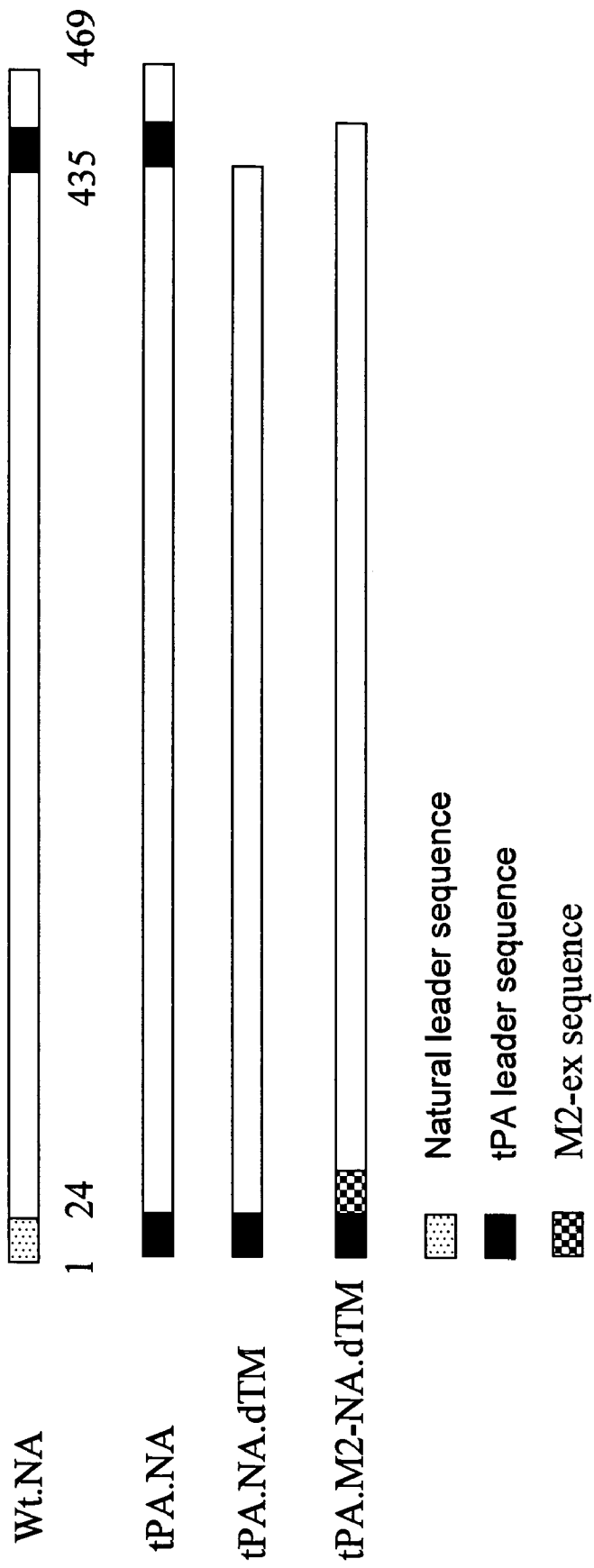

FIG. 9
Nucleotide sequence encoding H1 HA from Influenza A/New Caledonia/20/99 (See also
Genbank® Acc. No. AJ344014.1; GI No. 19849783).

```
ATGAAAGCAAAACTACTGGTCCTGTTATGTACATTTACAGCTACATATGCAGACACAATATGTATAGGCT
ACCATGCCAACAACTCAACCGACACTGTTGACACAGTACTTGAGAAGAATGTGACAGTGACACACTCTGT
CAACCTACTTGAGGACAGTCACAACGGAAAACTATGTCTACTAAAAGGAATAGCCCCACTACAATTGGGT
AATTGCAGCGTTGCCGGATGGATCTTAGGAAACCCAGAATGCGAATTACTGATTTCCAAGGAATCATGGT
CCTACATTGTAGAAACACCAAATCCTGAGAATGGAACATGTTACCCAGGGTATTTCGCCGACTATGAGGA
ACTGAGGGAGCAATTGAGTTCAGTATCTTCATTTGAGAGATTCGAAATATTCCCCAAAGAAAGCTCATGG
CCCAACCACACCGTAACCGGAGTATCAGCATCATGCTCCCATAATGGGAAAAGCAGTTTTTACAGAAATT
TGCTATGGCTGACGGGGAAGAATGGTTTGTACCCAAACCTGAGCAAGTCCTATGTAAACAACAAAGAGAA
AGAAGTCCTTGTACTATGGGGTGTTCATCACCCGCCTAACATAGGGGACCAAAGGGCCCTCTATCATACA
GAAAATGCTTATGTCTCTGTAGTGTCTTCACATTATAGCAGAAGATTCACCCCAGAAATAGCCAAAAGAC
CCAAAGTAAGAGATCAGGAAGGAAGAATCAACTACTACTGGACTCTGCTGGAACCTGGGGATACAATAAT
ATTTGAGGCAAATGGAAATCTAATAGCGCCATGGTATGCTTTTGCACTGAGTAGAGGCTTTGGATCAGGA
ATCATCACCTCAAATGCACCAATGGATGAATGTGATGCGAAGTGTCAAACACCTCAGGGAGCTATAAACA
GCAGTCTTCCTTTCCAGAATGTACACCCAGTCACAATAGGAGAGTGTCCAAAGTATGTCAGGAGTGCAAA
ATTAAGGATGGTTACAGGACTAAGGAACATCCCATCCATTCAATCCAGAGGTTTGTTTGGAGCCATTGCC
GGTTTCATTGAAGGGGGTGGACTGGAATGGTAGATGGGTGGTATGGTTATCATCATCAGAATGAGCAAG
GATCTGGCTATGCTGCAGATCAAAAAAGTACACAAAATGCCATTAACGGGATTACAAACAAGGTGAATTC
TGTAATTGAGAAAATGAACACTCAATTCACAGCTGTGGGCAAAGAATTCAACAAATTGGAAAGAAGGATG
GAAAACTTAAATAAAAAAGTTGATGATGGGTTTCTAGACATTTGGACATATAATGCAGAATTGTTGGTTC
TACTGGAAAATGAAAGGACTTTGGATTTCCATGACTCCAATGTGAAGAATCTGTATGAGAAAGTAAAAAG
CCAATTAAAGAATAATGCCAAAGAAATAGGAAACGGGTGTTTTGAATTCTATCACAAGTGTAACAATGAA
TGCATGGAGAGTGTGAAAAATGGAACTTATGACTATCCAAAATATTCCGAAGAATCAAAGTTAAACAGGG
AGAAAATTGATGGAGTGAAATTGGAATCAATGGGAGTCTATCAGATTCTGGCGATCTACTCAACTGTCGC
CAGTTCCCTGGTTCTTTTGGTCTCCCTGGGGGCAATCAGCTTCTGGATGTGTTCCAATGGGTCTTTGCAG
TGCAGAATATGC (SEQ ID NO:7)
```

FIG. 10
Nucleotide sequence encoding influenza A H3 HA nucleic acid sequence from Influenza A/ Panama/2007/99(H3N2)

ATGAAGACTATCATTGCTTTGAGCTACATTTTATGTCTGGTTTTCGCTCAAAAACTTCCCGGAAATGACAA
CAGCACGGCAACGCTGTGCCTGGGGCACCATGCAGTGTCAAACGGAACGCTAGTGAAAACAATCACGAATG
ACCAAATTGAAGTGACTAATGCTACTGAGCTGGTTCAGAGTTCCTCAACAGGTAGAATATGCGACAGTCCT
CACCAAATCCTTGATGGAGAAAACTGCACACTAATAGATGCTCTATTGGGAGACCCTCATTGTGATGGCTT
CCAAAATAAGGAATGGGACCTTTTTGTTGAACGCAGCAAAGCCTACAGCAACTGTTACCCTTATGATGTGC
CGGATTATGCCTCCCTTAGGTCACTAGTTGCCTCATCCGGCACACTGGAGTTTAACAATGAAAGCTTCAAT
TGGACTGGAGTCGCTCAGAATGGAACAAGCTCTGCTTGCAAAAGGAGATCTAATAAAAGTTTCTTTAGTAG
ATTGAATTGGTTGCACCAATTAAAATACAAATATCCAGCACTGAACGTGACTATGCCAAACAATGAAAAAT
TTGACAAATTGTACATTTGGGGGGTTCACCACCCGAGTACGGACAGTGACCAAATCAGCATATATGCTCAA
GCATCAGGGAGAGTCACAGTCTCTACCAAAAGAAGCCAACAAACTGTAATCCCGAATATCGGATCTAGACC
CTGGGTAAGGGGTGTCTCCAGCGGAATAAGCATCTATTGGACAATAGTAAAACCGGGAGACATACTTTTGA
TTAACAGCACAGGGAATCTAATTGCTCCTCGGGGTTACTTCAAAATACGAAGTGGGAAAAGCTCAATAATG
AGGTCAGATGCACCCATTGGCAAATGCAATTCTGAATGCATCACTCCAAATGGAAGCATTCCCAATGACAA
ACCATTTCAAAATGTAAACAGGATCACATATGGGGCCTGTCCCAGATATGTTAAGCAAAACACTCTGAAAT
TGGCAACAGGGATGCGGAATGTACCAGAGAAACAAACTAGAGGCATATTCGGCGCAATCGCGGGTTTCATA
GAAAATGGTTGGGAGGGAATGGTGGACGGTTGGTACGGTTTCAGGCATCAAAATTCTGAGGGCACAGGACA
AGCAGATCTTAAAAGCACTCAAGCAGCAATCAACCAAATCAACGGGAAACTGAATAGGTTAATCGAGAAAA
CGAACGAGAAATTCCATCAAATTGAAAAAGAATTCTCAGAAGTAGAAGGGAGAATTCAGGACCTCGAGAAA
TATGTTGAGGACACTAAAATAGATCTCTGGTCGTACAACGCGGAGCTTCTTGTTGCCCTGGAGAACCAACA
TACAATTGATCTAACTGACTCAGAAATGAACAAACTGTTTGAAAGAACAAAGAAGCAACTGAGGGAAAATG
CTGAGGATATGGGCAATGGTTGTTTCAAAATATACCACAAATGTGACAATGCCTGCATAGGGTCAATCAGA
AATGGAACTTATGACCATGATGTATACAGAGACGAAGCATTAAACAACCGGTTCCAGATCAAAGGTGTTGA
GCTGAAGTCAGGATACAAAGATTGGATCCTATGGATTTCCTTTGCCATATCATGCTTTTTGCTTTGTGTTG
TTTTGCTGGGGTTCATCATGTGGGCCTGCCAAAAAGGCAACATTAGGTGCAACATTTGCATTTGA (SEQ
ID NO:8)

FIG. 11.

Nucleotide sequence encoding NA from Influenza A/ Panama/2007/99(H3N2)(See GenBank® Acc. No. AJ457937.1, GI No. 22859354)

```
GCAAAAGCAGGAGTGAAAATGAATCCAAATCAAAAGATAATAACGATTGGCTCTGTTTCTCTCACTATTG
CCACAATATGCTTCCTTATGCAAATAGCCATCCTGGTAACTACTGTAACATTGCATTTCAAGCAATATGA
ATGCAACTCCCCCCCAAACAACCAAGTAATGCTGTGTGAACCAACAATAATAGAAAGAAACATAACAGAG
ATAGTGTATCTGACCAACACCACCATAGAGAAGGAAATATGCCCCAAACTAGCAGAATACAGAAATTGGT
CAAAGCCGCAATGTAAAATTACAGGATTTGCACCTTTTTCTAAGGATAATTCAATTCGGCTTTCCGCTGG
TGGGGACATTTGGGTGACAAGAGAACCTTATGTGTCATGCGATCCTGACAAGTGTTATCAATTTGCCCTT
GGACAGGGAACAACACTAAACAACAGGCATTCAAATGACACAGTACATGATAGGACCCCTTATCGAACCC
TATTGATGAATGAGTTGGGTGTTCCATTTCATTTGGGAACCAAGCAAGTGTGTATAGCATGGTCCAGCTC
AAGTTGTCACGATGGAAAAGCATGGCTGCATGTTTGTGTAACTGGGCATGATGAAAATGCAACTGCTAGC
TTCATTTACGATGGGAGACTTGTAGATAGTATTGGTTCATGGTCCAAAAAAATCCTCAGGACCCAGGAGT
CGGAATGCGTTTGTATCAATGGAACTTGTACAGTAGTAATGACTGATGGGAGTGCTTCAGGAAGAGCTGA
TACTAAAATACTTTTCATTGAGGAGGGGAAAATCGTTCATACTAGCAAATTGTCAGGAAGTGCTCAGCAT
GTCGAGGAGTGCTCCTGTTATCCTCGATATCCTGGTGTCAGATGTGTCTGCAGAGACAACTGGAAAGGCT
CCAATAGGCCCATCGTAGATATAAATGTAAAGGATTATAGCATTGTTTCCAGTTATGTGTGCTCAGGACT
TGTTGGAGACACACCCAGAAAAAACGACAGCTCCAGCAGTAGCCATTGCCTGGATCCTAACAATGAAGAA
GGGGGTCATGGAGTGAAAGGCTGGGCCTTTGATGATGGAAATGACGTGTGGATGGGAAGAACGATCAGCG
AGAAGTCACGCTCAGGTTATGAAACCTTCAAGGTCATTGAAGGCTGGTCCAAACCTAACTCCAAATTGCA
GATAAATAGGCAAGTCATAGTTGAAAGAGGTAATATGTCCGGTTATTCTGGTATTTTCTCTGTTGAAGGC
AAAAGCTGCATCAATCGGTGCTTTTATGTGGAGTTGATAAGGGGAAGGAAACAGGAAACTGAAGTCTGGT
GGACCTCAAACAGTATTGTTGTGTTTTGTGGCACCTCAGGTACATATGGAACAGGCTCATGGCCTGATGG
GGCGGACATCAATCTCATGCCTATATAAGCTTTCGCAATTTTAGAA     (SEQ ID NO:9)
```

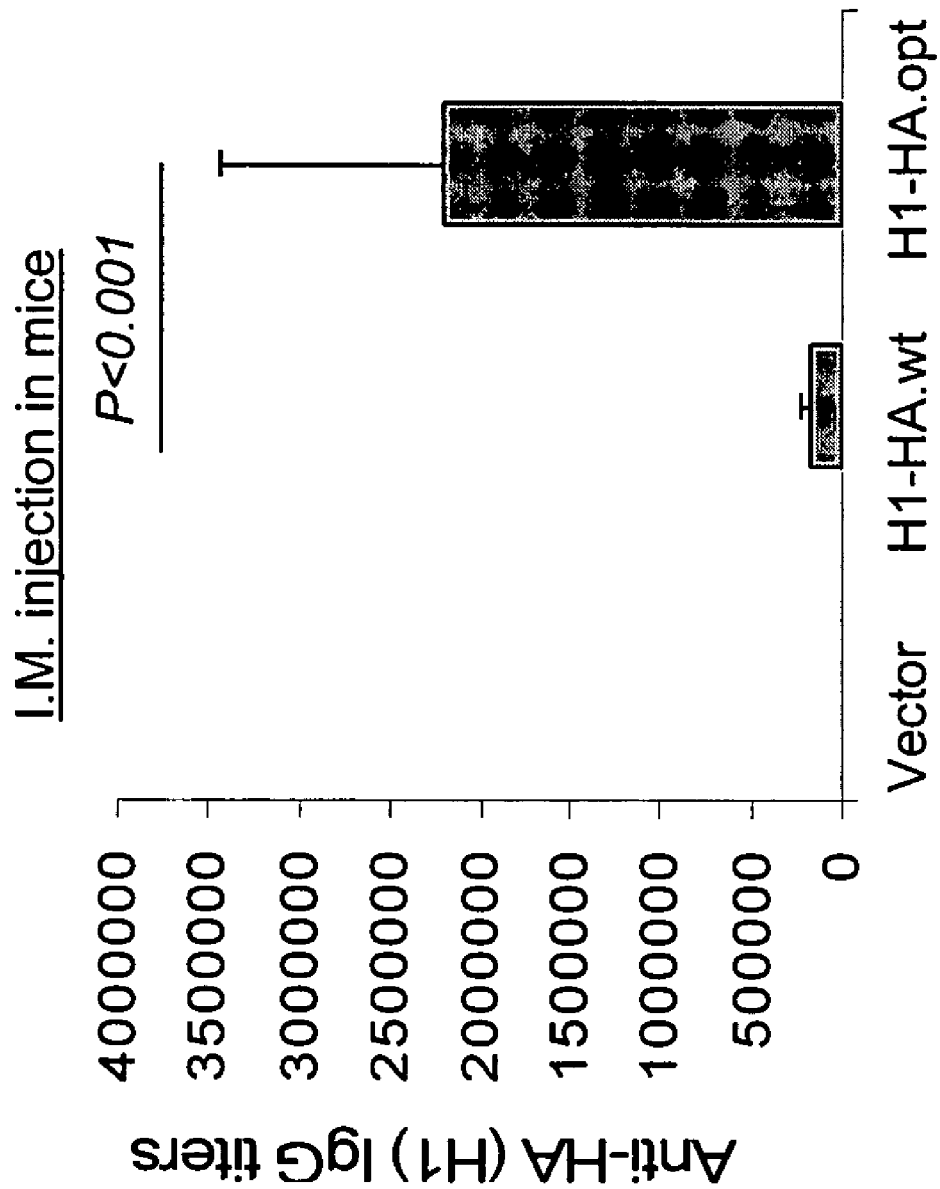

SEQUENCE LISTING

<160> NUMBER OF SEQ ID NOS: 9

<210> SEQ ID NO 1
<211> LENGTH: 1698
<212> TYPE: DNA
<213> ORGANISM: Artificial Sequence
<220> FEATURE:
<223> OTHER INFORMATION: Synthetically generated oligonucleotide

<400> SEQUENCE: 1

```
atgaaggcca agctgctggc cctgctgtgc accttcaccg ccacctacgc cgacaccatc      60
tgcatcggct accacgccaa caacagcacc gacaccgtgg ataccgtgct ggagaagaac     120
gtgacagtga cccacagcgt gaacctgctg gaggacagcc acaacggcaa gctgtgtctg     180
ctgaaaggca tcgcccccct gcagctgggc aactgtagcg tggccggctg gattctgggc     240
aaccccgaat gcgagctgct gatctccaag gagagctgga gctacatcgt ggagaccccc     300
aaccccgaga tggcacctg ctaccccggc tacttcgccg actacgagga gctgcgggag      360
cagctgagca gcgtgagcag cttcgagaga ttcgagatct cccccaagga aagcagctgg     420
cccaaccaca ccgtgaccgg agtgagcgcc agctgcagcc acaatgggaa gagcagcttc     480
tacagaaatc tgctgtggct gaccggcaag aacggcctgt accccaacct gagcaagtcc     540
tacgtgaaca acaaagagaa ggaagtgctg gtgctgtggg gcgtgcacca cccccctaac     600
atcggcaacc agcgggccct gtaccacacc gagaacgcct atgtgagcgt ggtgagcagc     660
cactacagca gaagattcac ccccgagatc gccaagagac ccaaagtgag agatcaggag     720
ggcagaatca actactactg gaccctgctg gagcccggcg acgccatcat cttcgaggcc     780
aacggcaacc tgatcgcccc ctggtacgcc ttcgccctga cagaggctt cggcagcggc     840
atcatcacca gcaatgcccc catggacgaa tgcgacgcca gtgtcagac accccagggc     900
gccatcaaca gcagcctgcc cttccagaac gtgcaccccg tgaccatcgg agagtgcccc     960
aagtacgtgc ggagcgccaa gctgcgcatg gtgaccggcc tgcggaacat ccccagcatt    1020
cagagcagag gcctgttcgg cgccatcgcc ggcttcatcg agggcggctg gaccggcatg    1080
gtggacggct ggtatggcta ccaccaccag aacgagcagg gatctggcta cgccgccgat    1140
cagaagagca cccagaacgc catcaacggc atcaccaaca agtgaacag cgtgatcgag    1200
aagatgaaca cccagttcac agccgtgggc aaggagttca caaaactgga gcggcggatg    1260
gaaaccctga acaagaaagt ggacgacggc ttcctggaca tctggaccta caacgccgag    1320
ctgctggtgc tgctggagaa tgagcggacc ctggacttcc acgacagcaa cgtgaagaac    1380
ctgtacgaga aagtgaagag ccagctgaag aacaacgcca aggagatcgg caacggctgc    1440
ttcgagttct accacaagtg caacaacgag tgcatggaga gcgtgaagaa cggcacctac    1500
gactacccca gtactccgga ggagagcaag ctgaaccggg agaagatcga cggcgtgaag    1560
ctggagagca tgggcgtgta ccagatcctg gccatctaca gcaccgtggc cagcagcctg    1620
gtgctgctgg tgagcctggg cgccatctct ttctggatgt gctccaacgg cagcctgcag    1680
tgcagaatct gcatctga                                                    1698
```

<210> SEQ ID NO 2
<211> LENGTH: 565
<212> TYPE: PRT
<213> ORGANISM: Artificial Sequence
<220> FEATURE:
<223> OTHER INFORMATION: Synthetically generated peptide

<400> SEQUENCE: 2

```
Met Lys Ala Lys Leu Leu Ala Leu Leu Cys Thr Phe Thr Ala Thr Tyr
  1               5                  10                  15

Ala Asp Thr Ile Cys Ile Gly Tyr His Ala Asn Asn Ser Thr Asp Thr
             20                  25                  30
```

-continued

```
Val Asp Thr Val Leu Glu Lys Asn Val Thr Val Thr His Ser Val Asn
         35                  40                  45

Leu Leu Glu Asp Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Thr Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
             115                 120                 125

Glu Arg Phe Glu Ile Phe Pro Lys Glu Ser Ser Trp Pro Asn His Thr
         130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Ala Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Thr Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
```

```
                    450                455                460
Val Lys Ser Gln Leu Lys Asn Asn Ala Lys Glu Ile Gly Asn Gly Cys
465                 470                475                480

Phe Glu Phe Tyr His Lys Cys Asn Asn Glu Cys Met Glu Ser Val Lys
                485                490                495

Asn Gly Thr Tyr Asp Tyr Pro Lys Tyr Ser Glu Glu Ser Lys Leu Asn
            500                505                510

Arg Glu Lys Ile Asp Gly Val Lys Leu Glu Ser Met Gly Val Tyr Gln
        515                520                525

Ile Leu Ala Ile Tyr Ser Thr Val Ala Ser Ser Leu Val Leu Leu Val
530                 535                540

Ser Leu Gly Ala Ile Ser Phe Trp Met Cys Ser Asn Gly Ser Leu Gln
545                 550                555                560

Cys Arg Ile Cys Ile
            565

<210> SEQ ID NO 3
<211> LENGTH: 1698
<212> TYPE: DNA
<213> ORGANISM: Artificial Sequence
<220> FEATURE:
<223> OTHER INFORMATION: Synthetically generated oligonucleotide

<400> SEQUENCE: 3
atgaaaacca tcatcgccct gagctacatc ctgtgcctgg tgttcgccca gaaactgccc      60
ggcaacgaca cagcaccgc caccctgtgt ctgggccacc acgccgtgag caacggcacc     120
ctggtgaaaa ccatcaccaa tgaccagatc gaagtgacca acgccaccga gctggtgcag     180
agcagcagca ccggcagaat ctgcgacagc cctcaccaga tcctggacgg cgagaactgt     240
accctgatcg acgccctgct gggagaccct cactgcgacg gcttccagaa caaggagtgg     300
gacctgttcg tggagcgcag caaggcctac agcaactgct acccttacga cgtgcccgac     360
tacgcctccc tgcggagcct ggtggccagc tctggcaccc tggagttcaa caacgagagc     420
ttcaattgga ccggcgtggc ccagaacggc accagcagcg cctgcaagcg gagaagcaac     480
aagagcttct tcagcagact gaactggctg caccagctga agtacaagta ccccgccctg     540
aacgtgacca tgcccaacaa cgaaaagttc gacaaactgt acatttgggg cgtgcaccac     600
cccagcaccg acagcgacca gatcagcatc tacgcccagg ccagcggcag agtgaccgtg     660
tctaccaaga gaagccagca gaccgtgatc cccaatatcg gcagcagacc ctgggtgcgg     720
ggcgtgtcca gcggaatctc catctactgg acaatcgtga agcccggcga catcctgctg     780
atcaactcca ccggcaacct gattgcccct cggggctact tcaagatccg gagcggcaaa     840
agcagcatca tgcggagcga tgcccccatc ggcaagtgca acagcgagtg catcaccccc     900
aacggcagca tccccaatga caagcccttc cagaacgtga accggatcac ctacggcgcc     960
tgccccagat acgtgaagca gaacaccctg aagctggcca caggaatgcg gaacgtgccc    1020
gagaagcaga cccggggcat cttcggcgcc atcgccggct tcatcgagaa tggctgggag    1080
ggcatggtgg acggctggta cggcttccgg caccagaaca cgagggcac cggacaggcc    1140 gacctgaaga gcacccaggc cgccatcaac cagatcaacg gcaagctgaa ccggctgatc    1200
gagaaaacca acgagaagtt ccaccagatc gagaaggagt cagcgaagt ggaaggcaga    1260 atccaggacc tggagaagta cgtggaggac accaagatcg atctgtggag ctacaacgcc    1320
gagctgctgg tcgccctgga gaaccagcac accatcgacc tgaccgactc cgagatgaac    1380
```

-continued

```
aaactgttcg agagaaccaa gaagcagctg cgggagaacg ccgaggacat gggcaacggc    1440
tgtttcaaga tctaccacaa gtgcgacaac gcctgcatcg gcagcatcag aaacggcacc    1500
tacgaccacg acgtgtacag agatgaggcc ctgaacaacc ggttccagat caagggcgtg    1560
gagctgaaga gcggctacaa ggattggatt ctgtggatct ccttcgccat cagctgcttc    1620
ctgctgtgcg tggtgctgct gggcttcatc atgtgggcct gtcagaaggg caacatccgg    1680
tgcaacatct gcatctga                                                  1698
```

<210> SEQ ID NO 4
<211> LENGTH: 565
<212> TYPE: PRT
<213> ORGANISM: Artificial Sequence
<220> FEATURE:
<223> OTHER INFORMATION: Synthetically generated peptide

<400> SEQUENCE: 4

```
Met Lys Thr Ile Ile Ala Leu Ser Tyr Ile Leu Cys Leu Val Phe Ala
  1               5                  10                  15

Gln Lys Leu Pro Gly Asn Asp Asn Ser Thr Ala Thr Leu Cys Leu Gly
             20                  25                  30

His His Ala Val Ser Asn Gly Thr Leu Val Lys Thr Ile Thr Asn Asp
         35                  40                  45

Gln Ile Glu Val Thr Asn Ala Thr Glu Leu Val Gln Ser Ser Ser Thr
     50                  55                  60

Gly Arg Ile Cys Asp Ser Pro His Gln Ile Leu Asp Gly Glu Asn Cys
 65                  70                  75                  80

Thr Leu Ile Asp Ala Leu Leu Gly Asp Pro His Cys Asp Gly Phe Gln
                 85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Arg Ser Asn
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Ser Thr Asp Ser Asp Gln Ile
        195                 200                 205

Ser Ile Tyr Ala Gln Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Gly Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300
```

-continued

```
Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
        340                 345                 350

Gly Phe Ile Glu Asn Gly Trp Glu Gly Met Val Asp Gly Trp Tyr Gly
    355                 360                 365

Phe Arg His Gln Asn Ser Glu Gly Thr Gly Gln Ala Asp Leu Lys Ser
370                 375                 380

Thr Gln Ala Ala Ile Asn Gln Ile Asn Gly Lys Leu Asn Arg Leu Ile
385                 390                 395                 400

Glu Lys Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ser Glu Met Asn Lys Leu Phe Glu
    450                 455                 460

Arg Thr Lys Lys Gln Leu Arg Glu Asn Ala Glu Asp Met Gly Asn Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Asp Val Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Leu Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565

<210> SEQ ID NO 5
<211> LENGTH: 1410
<212> TYPE: DNA
<213> ORGANISM: Artificial Sequence
<220> FEATURE:
<223> OTHER INFORMATION: Synthetically generated oligonucleotide

<400> SEQUENCE: 5
atgaacccca accagaagat catcaccatc ggcagcgtga gcctcaccat cgccaccgtg      60
tgcttcctca tgcagattgc catcctggtg accaccgtga cactgcactt caagcagtac     120
gagtgcgact ccccgccag caaccaggtg atgcctgcg agcccatcat catcgagcgg       180
aacatcaccg agatcgtgta cctgaacaac accaccatcg agaaagagat ctgccccaag     240
gtagtggagt accggaactg gagcaagccc cagtgccaga tcaccggctt tgccccttc      300 agcaaggaca cagcatccg gctgagcgct ggcggcgaca tctgggtgac cagagaaccc     360
tatgtgagct gcgaccacgg caagtgctac cagttcgccc tcggcagggg caccacactg     420
gacaacaagc acagcaatga caccatccac acagaatcc ctcaccgaac cctgctgatg      480
aacgagctgg gcgtgcccctt ccacctgggc acacggcaag tgtgcatcgc ctggtccagc     540
```

-continued

```
agcagctgcc acgatggcaa agcctggctg cacgtgtgca tcacaggcga cgacaagaat    600
gccaccgcca gcttcatcta cgacggccgg ctggtggaca gcattggcag ctggagccag    660
aacatcctcc ggacccagga gagcgagtgc gtgtgcatca atggcacctg caccgtggtg    720
atgaccgacg gcagcgccag cggcagagcc gacacaagaa tcctgttcat cgaggagggc    780
aagatcgtcc acatcagccc cctgagcggc agcgcccagc acgtggaaga gtgctcctgc    840
tatccccggt accctggcgt ccggtgcatc tgtagagaca actggaaggg cagcaaccgg    900
cccgtggtgg acatcaacat ggaggactac agcatcgact ccagctacgt gtgcagcggc    960
ctggtgggcg acacaccccg gaacgacgac cggagcagca cagcaactg ccggaacccc    1020 aacaatgaga gaggcaacca aggagtgaag ggctgggcct cgacaatgg cgatgacgtg    1080 tggatgggcc ggaccatcag caaggacctg cgcagcggct acgagacctt caaggtgatt    1140
ggcggctggt ccaccccca ctccaagagc cagatcaaca gacaggtgat cgtggacagc    1200
gacaaccgga gcggctacag cggcatcttc agcgtggagg gcaagagctg catcaaccgg    1260
tgcttctacg tggagctgat ccggggccgg aagcaggaga ccagagtgtg gtggaccagc    1320
aacagcatcg tggtgttctg tggcaccagc ggcacctacg gcaccggcag ctggcctgat    1380
ggcgccaaca tcaacttcat gcccatctaa    1410
```

<210> SEQ ID NO 6
<211> LENGTH: 469
<212> TYPE: PRT
<213> ORGANISM: Artificial Sequence
<220> FEATURE:
<223> OTHER INFORMATION: Synthetically generated peptide

<400> SEQUENCE: 6

```
Met Asn Pro Asn Gln Lys Ile Ile Thr Ile Gly Ser Val Ser Leu Thr
  1               5                  10                  15

Ile Ala Thr Val Cys Phe Leu Met Gln Ile Ala Ile Leu Val Thr Thr
             20                  25                  30

Val Thr Leu His Phe Lys Gln Tyr Glu Cys Asp Ser Pro Ala Ser Asn
         35                  40                  45

Gln Val Met Pro Cys Glu Pro Ile Ile Ile Glu Arg Asn Ile Thr Glu
     50                  55                  60

Ile Val Tyr Leu Asn Asn Thr Thr Ile Glu Lys Glu Ile Cys Pro Lys
 65                  70                  75                  80

Val Val Glu Tyr Arg Asn Trp Ser Lys Pro Gln Cys Gln Ile Thr Gly
                 85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Gly Lys
        115                 120                 125

Cys Tyr Gln Phe Ala Leu Gly Gln Gly Thr Thr Leu Asp Asn Lys His
    130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asp
        195                 200                 205
```

-continued

```
Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
                260                 265                 270

Gln His Val Glu Glu Cys Ser Cys Tyr Pro Arg Tyr Pro Gly Val Arg
            275                 280                 285

Cys Ile Cys Arg Asp Asn Trp Lys Gly Ser Asn Arg Pro Val Val Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
                325                 330                 335

Cys Arg Asn Pro Asn Asn Glu Arg Gly Asn Gln Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465

<210> SEQ ID NO 7
<211> LENGTH: 1692
<212> TYPE: DNA
<213> ORGANISM: Influenza A virus (A/NewCaledonia/20/1999(H1N1)

<400> SEQUENCE: 7
atgaaagcaa aactactggt cctgttatgt acatttacag ctacatatgc agacacaata      60
tgtataggct accatgccaa caactcaacc gacactgttg acacagtact tgagaagaat     120
gtgacagtga cacactctgt caacctactt gaggacagtc acaacggaaa actatgtcta     180
ctaaaaggaa tagccccact acaattgggt aattgcagcg ttgccggatg gatcttagga     240
aacccagaat gcgaattact gatttccaag gaatcatggt cctacattgt agaaacacca     300
aatcctgaga atggaacatg ttacccaggg tatttcgccg actatgagga actgagggag     360
caattgagtt cagtatcttc atttgagaga ttcgaaatat ccccaagaa aagctcatgg     420 cccaaccaca ccgtaaccgg agtatcagca tcatgctccc ataatgggaa aagcagtttt     480
tacagaaatt tgctatggct gacggggaag aatggtttgt acccaaacct gagcaagtcc     540
tatgtaaaca caaagagaa agaagtcctt gtactatggg gtgttcatca cccgcctaac     600
```

| | |
|---|---:|
| ataggggacc aaagggccct ctatcataca gaaaatgctt atgtctctgt agtgtcttca | 660 |
| cattatagca gaagattcac cccagaaata gccaaaagac ccaaagtaag agatcaggaa | 720 |
| ggaagaatca actactactg gactctgctg gaacctgggg atacaataat atttgaggca | 780 |
| aatggaaatc taatagcgcc atggtatgct tttgcactga gtagaggctt tggatcagga | 840 |
| atcatcacct caaatgcacc aatggatgaa tgtgatgcga agtgtcaaac acctcaggga | 900 |
| gctataaaca gcagtcttcc tttccagaat gtacacccag tcacaatagg agagtgtcca | 960 |
| aagtatgtca ggagtgcaaa attaaggatg gttacaggac taaggaacat cccatccatt | 1020 |
| caatccagag gtttgtttgg agccattgcc ggtttcattg aagggggtg gactggaatg | 1080 |
| gtagatgggt ggtatggtta tcatcatcag aatgagcaag gatctggcta tgctgcagat | 1140 |
| caaaaaagta cacaaaatgc cattaacggg attacaaaca aggtgaattc tgtaattgag | 1200 |
| aaaatgaaca ctcaattcac agctgtgggc aaagaattca acaaattgga agaaggatg | 1260 |
| gaaaacttaa ataaaaaagt tgatgatggg tttctagaca tttggacata taatgcagaa | 1320 |
| ttgttggttc tactggaaaa tgaaaggact ttggatttcc atgactccaa tgtgaagaat | 1380 |
| ctgtatgaga aagtaaaaag ccaattaaag aataatgcca agaaatagg aaacgggtgt | 1440 |
| tttgaattct atcacaagtg taacaatgaa tgcatggaga gtgtgaaaaa tggaacttat | 1500 |
| gactatccaa atattccga agaatcaaag ttaaacaggg agaaaattga tggagtgaaa | 1560 |
| ttggaatcaa tgggagtcta tcagattctg gcgatctact caactgtcgc cagttccctg | 1620 |
| gttcttttgg tctccctggg ggcaatcagc ttctggatgt gttccaatgg gtctttgcag | 1680 |
| tgcagaatat gc | 1692 |

<210> SEQ ID NO 8
<211> LENGTH: 1698
<212> TYPE: DNA
<213> ORGANISM: Influenza A virus (A/Panama/2007/1999(H3N2))

<400> SEQUENCE: 8

| | |
|---|---:|
| atgaagacta tcattgcttt gagctacatt ttatgtctgg ttttcgctca aaaacttccc | 60 |
| ggaaatgaca acagcacggc aacgctgtgc ctggggcacc atgcagtgtc aaacggaacg | 120 |
| ctagtgaaaa caatcacgaa tgaccaaatt gaagtgacta atgctactga gctggttcag | 180 |
| agttcctcaa caggtagaat atgcgacagt cctcaccaaa tccttgatgg agaaaactgc | 240 |
| acactaatag atgctctatt gggagaccct cattgtgatg gcttccaaaa taaggaatgg | 300 |
| gaccttttg ttgaacgcag caaagcctac agcaactgtt acccttatga tgtgccggat | 360 |
| tatgcctccc ttaggtcact agttgcctca tccggcacac tggagtttaa caatgaaagc | 420 |
| ttcaattgga ctggagtcgc tcagaatgga acaagctctg cttgcaaaag agatctcaat | 480 |
| aaaagtttct ttagtagatt gaattggttg caccaattaa atacaaaata tccagcactg | 540 |
| aacgtgacta tgccaaacaa tgaaaaattt gacaaattgt acatttgggg ggttcaccac | 600 |
| ccgagtacgg acagtgacca atcagcata tatgctcaag catcagggag agtcacagtc | 660 |
| tctaccaaaa gaagccaaca aactgtaatc ccgaatatcg gatctagacc ctgggtaagg | 720 |
| ggtgtctcca gcggaataag catctattgg acaatagtaa accgggaga catacttttg | 780 |
| attaacagca cagggaatct aattgctcct cggggttact tcaaaatacg aagtgggaaa | 840 |
| agctcaataa tgaggtcaga tgcacccatt ggcaaatgca attctgaatg catcactcca | 900 |
| aatggaagca ttcccaatga caaaccattt caaaatgtaa acaggatcac atatgggcc | 960 |
| tgtcccagat atgttaagca aaacactctg aaattggcaa cagggatgcg aatgtacca | 1020 |

-continued

```
gagaaacaaa ctagaggcat attcggcgca atcgcgggtt tcatagaaaa tggttgggag      1080
ggaatggtgg acggttggta cggtttcagg catcaaaatt ctgagggcac aggacaagca      1140
gatcttaaaa gcactcaagc agcaatcaac caaatcaacg ggaaactgaa taggttaatc      1200
gagaaaacga acgagaaatt ccatcaaatt gaaaagaat tctcagaagt agaagggaga       1260
attcaggacc tcgagaaata tgttgaggac actaaaatag atctctggtc gtacaacgcg      1320
gagcttcttg ttgccctgga gaaccaacat acaattgatc taactgactc agaaatgaac      1380
aaactgtttg aaagaacaaa gaagcaactg agggaaaatg ctgaggatat gggcaatggt      1440
tgtttcaaaa tataccacaa atgtgacaat gcctgcatag ggtcaatcag aaatggaact      1500
tatgaccatg atgtatacag agacgaagca ttaaacaacc ggttccagat caaaggtgtt      1560
gagctgaagt caggatacaa agattggatc ctatggattt cctttgccat atcatgcttt      1620
ttgctttgtg ttgttttgct ggggttcatc atgtgggcct gccaaaaagg caacattagg      1680
tgcaacattt gcatttga                                                    1698

<210> SEQ ID NO 9
<211> LENGTH: 1446
<212> TYPE: DNA
<213> ORGANISM: Influenza A virus (A/Panama/2007/1999(H3N2))

<400> SEQUENCE: 9
gcaaaagcag gagtgaaaat gaatccaaat caaaagataa taacgattgg ctctgtttct       60
ctcactattg ccacaatatg cttccttatg caaatagcca tcctggtaac tactgtaaca      120
ttgcatttca gcaatatga atgcaactcc cccccaaaca accaagtaat gctgtgtgaa       180
ccaacaataa tagaaagaaa cataacagag atagtgtatc tgaccaacac caccatagag      240
aaggaaatat gccccaaact agcagaatac agaaattggt caaagccgca atgtaaaatt      300
acaggatttg caccttttttc taaggataat tcaattcggc tttccgctgg tggggacatt      360
tgggtgacaa gagaacctta tgtgtcatgc gatcctgaca gtgttatca atttgccctt       420 ggacagggaa caacactaaa caacaggcat tcaaatgaca cagtacatga taggacccct      480
tatcgaaccc tattgatgaa tgagttgggt gttccatttc atttgggaac caagcaagtg      540
tgtatagcat ggtccagctc aagttgtcac gatggaaaag catggctgca tgtttgtgta      600
actgggcatg atgaaaatgc aactgctagc ttcatttacg atgggagact tgtagatagt      660
attggttcat ggtccaaaaa aatcctcagg acccaggagt cggaatgcgt tgtatcaat       720 ggaacttgta cagtagtaat gactgatggg agtgcttcag gaagagctga tactaaaata      780 ctttttcattg aggaggggaa aatcgttcat actagcaaat tgtcaggaag tgctcagcat      840
gtcgaggagt gctcctgtta tcctcgatat cctggtgtca atgtgtctg cagagacaac       900 tggaaaggct ccaataggcc catcgtagat ataaatgtaa aggattatag cattgtttcc      960
agttatgtgt gctcaggact tgttggagac acacccagaa aaaacgacag ctccagcagt     1020
agccattgcc tggatcctaa caatgaagaa gggggtcatg gagtgaaagg ctgggccttt      1080
gatgatggaa atgacgtgtg gatgggaaga acgatcagcg agaagtcacg ctcaggttat     1140
gaaaccttca aggtcattga aggctggtcc aaacctaact ccaaattgca gataaatagg     1200
caagtcatag ttgaaagagg taatatgtcc ggttattctg gtattttctc tgttgaaggc     1260
aaaagctgca tcaatcggtg cttttatgtg gagttgataa ggggaaggaa acaggaaact     1320
gaagtctggt ggaccttcaa cagtattgtt gtgttttgtg gcacctcagg tacatatgga     1380
```

```
-continued acaggctcat ggcctgatgg ggcggacatc aatctcatgc ctatataagc tttcgcaatt    1440
ttagaa                                                                1446
```

INFLUENZA NUCLEIC ACIDS, POLYPEPTIDES, AND USES THEREOF

CROSS-REFERENCE TO RELATED APPLICATIONS

This application claims the benefit of priority of U.S. Provisional Application No. 60/655,979, filed on Feb. 24, 2005, the entire contents of which are hereby incorporated by reference.

TECHNICAL FIELD

This invention relates to viral nucleic acid sequences, proteins, and subunit (both nucleic acid and recombinant protein) vaccines and more particularly to viral nucleic acids sequences that have been optimized for expression in mammalian host cells.

BACKGROUND

Influenza virus is a worldwide public health problem. Influenza causes, on average, 20,000 deaths and many more thousands of hospitalizations annually in the United States alone (Palese and Garcia-Sastre, *J. Clin. Invest.*, 110(1): 9-12, 2002). Vaccination is recommended for nearly half of the population of the United States (Couch, *Ann. Intern. Med.*, 133: 992-998, 2000). Influenza also causes the death of thousands of domestic animals annually.

The effectiveness of currently available vaccines depends on the degree to which the vaccine antigens match those of the circulating influenza strains. Immune responses to an antigen of a particular type of influenza may be poorly cross-reactive with the antigen encoded by a second type of influenza. Influenza viruses have the tendency to undergo antigenic changes, complicating efforts to produce effective vaccines. Antigenic shift, which occurs when genes from different influenza types reassort in infected hosts, is one mechanism by which dramatic antigenic variation occurs. Antigenic shift occurs in influenza A types, which circulate among humans and animals. Influenza B types are more restricted to humans and are not thought to undergo antigenic shift (Palese and Garcia-Sastre, *J. Clin. Invest.*, 110(1): 9-12, 2002). Antigenic drift is a second, less drastic mechanism, in which viral genes accumulate mutations over time. Both types of antigenic variation increase the difficulty of generating vaccines effective for protection against a broad range of influenza strains.

SUMMARY

We have discovered that codon-optimized forms of nucleic acids encoding influenza polypeptides such as influenza hemagglutinin (HA), neuraminidase (NA), or membrane ion channel (M2), are useful for expressing such polypeptides in appropriate host cells. Codon-optimization permits more efficient expression than expression achieved using codons native to the virus. Enhanced expression is useful for producing large quantities of polypeptides for therapeutic and diagnostic applications. Nucleic acids encoding influenza antigens that are efficiently expressed in mammalian host cells are useful, e.g., for inducing immune responses to the antigens in the host. The nucleic acid sequences described herein may induce higher levels of specific antibodies to an influenza antigen when administered to an animal (as compared to nucleic acid sequences which are not codon-optimized). In various embodiments, the nucleic acid sequences induce hemagglutination inhibiting, and/or virus-neutralizing antibodies when expressed in a mammalian subject.

Furthermore, viral proteins produced in mammalian cells can fold properly, oligomerize with natural binding partners, and/or can possess native post-translational modifications such as glycosylation. These features can enhance immunogenicity, thereby increasing protection afforded by vaccination with the proteins (or with the nucleic acids encoding the proteins). Codon-optimized nucleic acids can be constructed by synthetic means, obviating the need to obtain nucleic acids from live virus and/or increasing the ease of manipulation of sequences.

We have also discovered novel polyvalent and multi-component compositions for use in inducing immune responses. Multi-component compositions include or encode multiple different influenza polypeptides, or antigenic fragments thereof, e.g., they include or encode HA, NA, and/or M2. Polyvalent compositions include or encode multiple forms of a single antigen from different subtypes, such as HA from subtypes H1, H2, H3, H5, H7, and/or H9.

Accordingly, in one aspect, the invention features isolated nucleic acid molecules that include a sequence encoding an influenza polypeptide or an antigenic fragment thereof, wherein all or part of the sequence has been codon-optimized for expression in a host cell (e.g., a eukaryotic cell, e.g., a mammalian cell, such as a human cell). In various embodiments, more than 5%, 10%, 20%, 30%, 40%, 50%, 60%, 70%, 80%, 85%, 87%, 90%, 92%, 95%, 97%, 98%, 99%, or 100% of the codons in the sequence are mutated, relative to the codons in a wild-type viral sequence, to codons common to mammalian genes.

For example, isolated nucleic acid molecules that include a codon-optimized sequence encoding an influenza type hemagglutinin (HA) polypeptide or an antigenic fragment thereof are provided herein. In one embodiment, the sequence has been codon-optimized for expression in a human cell. The sequence can encode, e.g., an influenza type B HA polypeptide or an influenza type A HA polypeptide, e.g., selected from the following subtypes: H1, H2, H3, H4, H5, H6, H7, H8, H9, H10, H11, H12, H13, H14, and H15.

The sequences can encode an HA polypeptide of the H1 subtype, e.g., wherein the sequence is at least 70%, 80%, 85%, 87%, 90%, 92%, 95%, 97%, 98%, 99%, or 100% identical to SEQ ID NO:1 or to a fragment thereof containing at least 30 contiguous nucleotides of SEQ ID NO:1. The sequence can encode an HA polypeptide of the H3 subtype, e.g., wherein the sequence is at least 70%, 80%, 85%, 87%, 90%, 92%, 95%, 97%, 98%, 99%, or 100% identical to SEQ ID NO:3 or to a fragment thereof containing at least 30 contiguous nucleotides of SEQ ID NO:3. The sequence can further encode a leader peptide, e.g., a leader peptide that is not naturally associated with the influenza HA polypeptide, e.g., a mammalian leader peptide, e.g., a tissue plasminogen activator (tPA) leader peptide.

The fragment of an HA polypeptide encoded by the sequence can include, e.g., an HA1 domain of the HA polypeptide, an HA2 domain of the HA polypeptide, or an extracellular portion of HA.

The sequences encoding the HA polypeptide differ from naturally-occurring viral HA sequences. For example, a codon-optimized sequence encoding H1 HA can differ from SEQ ID NO:7 by at least 5, 10, 15, 20, 25, 50, 100, or 150 nucleotides. In some embodiments, the codon-optimized sequence encoding H1 HA differs from SEQ ID NO:7 by fewer than 400, 350, 300, or 250 nucleotides. In another example, the codon-optimized sequence encoding H3 HA can differ from SEQ ID NO:8 by at least 5, 10, 15, 20, 25, 50, 100, or 150 nucleotides. In some embodiments, the codon-optimized sequence encoding H3 HA differs from a SEQ ID NO:8 by fewer than 400, 350, 300, or 250 nucleotides. The codon-optimized sequences can encode polypeptides that are 95%, 97%, 98%, 99%, or 100% identical to polypeptides encoded by a naturally-occurring viral sequence.

In some embodiments, the isolated nucleic acid molecule encoding an influenza type A HA polypeptide or an antigenic fragment thereof includes SEQ ID NO:1 and/or SEQ ID NO:3.

In another aspect, the invention features isolated nucleic acid molecules that include a sequence encoding an influenza neuraminidase (NA) polypeptide or an antigenic fragment thereof, wherein the sequence has been codon-optimized for expression in a human cell. The sequences encode, e.g., an influenza type B NA polypeptide or an influenza type A NA polypeptide, e.g., selected from the following subtypes: N1, N2, N3, N4, N5, N6, N7, N8, and N9.

In one embodiment, the sequence encodes an NA polypeptide of the N2 subtype, e.g., wherein the sequence is at least 70%, 80%, 85%, 87%, 90%, 92%, 95%, 97%, 98%, 99%, or 100% identical to SEQ ID NO:5. The sequence can further encode a leader peptide, e.g., a leader peptide that is not naturally associated with the influenza NA polypeptide, e.g., a mammalian leader peptide, e.g., a tissue plasminogen activator (tPA) leader peptide.

The sequences encoding the NA polypeptide differ from naturally-occurring viral NA sequences. For example, a codon-optimized sequence encoding NA can differ from SEQ ID NO:9 by at least 5, 10, 15, 20, 25, 50, 100, or 150 nucleotides. In some embodiments, the codon-optimized sequence encoding NA differs from SEQ ID NO:9 by fewer than 350, 300, 250, or 200 nucleotides.

In one embodiment, the isolated nucleic acid molecule encoding an NA polypeptide or an antigenic fragment thereof includes SEQ ID NO:5.

Also provided herein are isolated nucleic acid molecules that include a sequence encoding two or more copies of an extracellular portion of an influenza M2 polypeptide, e.g., wherein the two or more copies of the extracellular portion of the M2 polypeptide are expressed as a single fusion polypeptide. Also provided are codon-optimized sequences encoding the M2 polypeptide and fusions containing two or more copies of the M2 polypeptide. The M2 sequences can further include a second sequence encoding an influenza HA or NA polypeptide as a fusion with the two or more copies of the extracellular portion of the M2 polypeptide.

The nucleic acid molecules described herein can be operably linked to a promoter. Also provided herein are nucleic acid expression vectors that include one or more nucleic acid molecule described herein. Also provided are compositions that include a nucleic acid molecule described herein and a mammalian promoter operably linked to the nucleic acid molecule, wherein the promoter directs transcription of mRNA encoding the influenza polypeptide (e.g., a cytomegalovirus immediate-early promoter); and a mammalian polyadenylation signal (e.g., a polyadenylation signal derived from a bovine growth hormone gene) operably linked to the nucleic acid molecule. The compositions can further include an adjuvant and/or a pharmaceutically acceptable carrier. In some embodiments, the compositions further include particles to which the isolated nucleic acid is bound, e.g., wherein the particles are suitable for gene gun, intradermal, intramuscular, or mucosal administration.

Also provided are cells that include one or more of the nucleic acids described herein. The cells are, e.g., eukaryotic, e.g., mammalian, e.g., human.

In another aspect, the invention features polypeptides encoded by the nucleic acid molecules described herein, e.g., wherein the polypeptide is produced in a mammalian cell such as a human cell. Also provided are isolated antibodies or antigen binding fragments thereof that specifically bind to the polypeptides. The antibodies can be polyclonal or monoclonal antibodies.

In yet another aspect, the invention features nucleic acid compositions that include various combinations of sequences. For example, a composition can include (a) a first sequence encoding a first type of influenza polypeptide (e.g., HA) of a first influenza subtype; and (b) a second sequence encoding the first type of influenza polypeptide of a second influenza subtype. The first and second sequences encode, for example, HA polypeptides or antigenic fragments thereof, NA polypeptides or antigenic fragments thereof, or M2 polypeptides or antigenic fragments thereof. In various embodiments, both the first and second influenza subtypes are influenza A subtypes (e.g., the first subtype is influenza A H1N1 and the second subtype is influenza A H3N2); both the first and second influenza subtypes are influenza B subtypes; or the first influenza subtype is an influenza A subtype and the second influenza subtype is an influenza B subtype. One or both sequences can be codon-optimized for expression in a mammalian cell. For example, the composition can include a sequence at least 90% identical to SEQ ID NO:1, SEQ ID NO:3, or SEQ ID NO:5. In one embodiment, the composition includes a sequence at least 90%, 95%, 97%, or 99% identical to SEQ ID NO:1 and a sequence at least 90%, 95%, 97%, or 99% identical to SEQ ID NO:3. In some embodiments, the composition further includes a sequence encoding the first type of influenza polypeptide of a third influenza subtype.

In some embodiments, the composition further includes a sequence encoding a second type of influenza polypeptide. For example, the composition can include a sequence encoding an HA polypeptide of a first and second subtype (e.g., H1 HA and H3 HA) and also a sequence encoding an NA polypeptide.

In some embodiments, the nucleic acid composition further includes one or more types of influenza polypeptides (e.g., one or more of HA, NA, and M2). In some embodiments, the composition further includes a second composition including influenza virions, e.g., live and/or inactivated virions. In various embodiments, the second composition includes two or more types of influenza virions, e.g., three types of influenza virions, e.g., inactivated influenza A H1N1 virions, inactivated influenza A H3N2 virions, and inactivated influenza B virions.

Also provided are pharmaceutical compositions including a nucleic acid composition described herein. The compositions can further include an adjuvant.

In another aspect, the invention features nucleic acid compositions including (a) a sequence encoding a first influenza polypeptide of a first influenza subtype; and (b) a sequence encoding a second influenza polypeptide of the first influenza subtype or a second influenza subtype; wherein the sequence of (a) and the sequence of (b) have been codon-optimized for expression in a mammalian cell. For example, the first and second influenza polypeptides are selected from a hemagglutinin (HA) polypeptide or antigenic fragment thereof, an influenza neuraminidase (NA) polypeptide or antigenic fragment thereof, or an influenza membrane ion channel (M2) polypeptide. In some embodiments, the composition further includes a sequence encoding a third influenza polypeptide. In one embodiment, the first polypeptide is an influenza HA polypeptide with a sequence at least 90%, e.g., 95%, 97%, 98%, 99%, or 100% identical to SEQ ID NO:1, SEQ ID NO:3, or SEQ ID NO:5.

The composition can further include one or more types of influenza polypeptides, e.g., the composition further includes a composition comprising influenza virions, e.g., live and/or inactivated virions. The composition can include other features described herein.

The invention also features methods for inducing an immune response to one or more influenza polypeptides in a subject (e.g., a subject in need of treatment for, or a subject at risk for exposure to, influenza). The methods include, for example, administering to the subject a composition described herein, wherein the composition is administered in an amount sufficient for the sequence to express the one or more influenza polypeptides at a level sufficient to induce an immune response in the subject. The methods can further include administering to the subject a second composition comprising an influenza polypeptide. In one embodiment, the second composition comprises influenza virions, e.g., live and/or inactivated virions, e.g., live, attenuated virions. In one embodiment, two or more types of influenza virions, e.g., three types of, e.g., inactivated, influenza virions, are administered. In one embodiment, the three types of influenza virions are inactivated influenza A H1N1 virions, inactivated influenza A H3N2 virions, and inactivated influenza B virions. The second composition can be administered simultaneously with, before, or after the first composition.

Also provided herein are methods for producing an influenza polypeptide. The methods include providing a nucleic acid molecule described herein; and expressing the nucleic acid in a host cell (e.g., a mammalian cell, e.g., a human cell) under conditions in which the influenza polypeptide encoded by the nucleic acid molecule is produced. The method can further include isolating a composition comprising the influenza polypeptide from the cells.

In order that the present invention may be more readily understood, certain terms are first defined. Additional definitions are set forth throughout the detailed description.

A "subunit" vaccine is a vaccine whose active ingredient antigen is only part of a pathogen, e.g., one protein or a fragment of such protein in a pathogen with multiple proteins.

A "nucleic acid vaccine" is a vaccine whose active ingredient is at least one isolated nucleic acid that encodes a polypeptide antigen.

A "recombinant protein vaccine" is a vaccine whose active ingredient is at least one protein antigen that is produced by recombinant expression.

An "isolated nucleic acid" is a nucleic acid free of the genes that flank the gene of interest in the genome of the organism or virus in which the gene of interest naturally occurs. The term therefore includes a recombinant DNA incorporated into an autonomously expressing plasmid in mammalian systems. It also includes a separate molecule such as a cDNA, a genomic fragment, a fragment produced by polymerase chain reaction, or a restriction fragment. It also includes a recombinant nucleotide sequence that is part of a hybrid gene, i.e., a gene encoding a fusion protein. An isolated nucleic acid is substantially free of other cellular or viral material (e.g., free from the protein components of a viral vector), or culture medium when produced by recombinant techniques, or substantially free of chemical precursors or other chemicals when chemically synthesized.

Expression control sequences are "operably linked" to a gene of interest when they are incorporated into other nucleic acids so that they effectively control expression of the gene.

An "adjuvant" is a compound or mixture of compounds that enhances the ability of a nucleic acid composition and/or a polypeptide composition to elicit an immune response in a subject.

A "mammalian promoter" is any nucleic acid sequence, regardless of origin, that is capable of driving transcription of an mRNA coding for a polypeptide within a mammalian cell.

A "mammalian polyadenylation signal" is any nucleic acid sequence, regardless of origin, that is capable of terminating transcription of an mRNA encoding a polypeptide within a mammalian cell.

"Protein" is used interchangeably with "polypeptide," and includes both polypeptides produced in vitro and polypeptides expressed in vivo after nucleic acid sequences are administered into the host animals or human subjects." "Polypeptide" refers to any chain of amino acids, regardless of length or post-translational modification (e.g., glycosylation or phosphorylation).

An "anti-influenza antibody" is an antibody that specifically interacts with (e.g., specifically binds to) an influenza antigen, e.g., HA or NA.

As used herein, the term "treat" or "treatment" is defined as the application or administration of a nucleic acid encoding an influenza antigen, or fragment thereof, or anti-influenza antibodies to a subject, e.g., a patient, or application or administration to an isolated tissue or cell from a subject, e.g., a patient, which is returned to the patient. Treatment also covers the administration of polypeptides encoded by the nucleic acids, or antibodies that specifically bind to the polypeptides. The nucleic acids can be administered alone or in combination with a second agent. The subject can be a patient having influenza, a symptom of influenza, a predisposition toward influenza, or a patient who is at risk for contracting an influenza infection. The treatment can cure, heal, alleviate, relieve, alter, remedy, ameliorate, palliate, improve, or affect the infection or symptoms of influenza.

As used herein, an amount of a nucleic acid, protein, or an anti-influenza antibody effective to treat a disorder, or a "therapeutically effective amount," refers to an amount that is effective, upon single or multiple dose administration to a subject, in treating a subject with influenza. As used herein, an amount of a nucleic acid, protein, or an anti-influenza antibody effective to prevent or inhibit infection with, and/or disease caused by influenza, or a "a prophylactically effective amount," of the antibody refers to an amount which is effective, upon single- or multiple-dose administration to the subject, in inhibiting or delaying the occurrence of the onset or recurrence of influenza, or reducing a symptom (e.g., reducing the severity of a symptom) thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes. U.S. Provisional App. No. 60/655,979 is incorporated by reference in its entirety for all purposes.

BRIEF DESCRIPTION OF THE DRAWINGS

FIG. 1A is a representation of a codon optimized influenza A H1 HA nucleic acid sequence (SEQ ID NO:1). The boundaries for each domain encoded within the sequences are as follows: nucleotides 1-69 encode the leader peptide; 70-1032 encode the HA1 domain; 1033-1695 encode the HA2 domain; 1585-1653 encode the membrane domain; 1654-1695 encode the cytoplasmic domain.

FIG. 1B is a representation of the influenza A H1 HA amino acid sequence (SEQ ID NO:2) encoded by the nucleic acid sequence in FIG. 1A. Amino acids 1-23 correspond to the leader sequences; 24-344 correspond to the HA1 domain; 345-565 correspond to the HA2 domain; 529-551 correspond to the transmembrane domain; and 552-565 correspond to the cytoplasmic domain.

FIG. 2A is a representation of a codon optimized influenza A H3 HA nucleic acid sequence (SEQ ID NO:3). The boundaries for each domain encoded within the sequences are as follows: 1-63 encode the leader peptide; 64-1035 encode the HA1 domain; 1036-1695 encode the HA2 domain; 1585-1653 encode the transmembrane domain; 1654-1695 encode the cytoplasmic domain.

FIG. 2B is a representation of the influenza A H3 HA amino acid sequence (SEQ ID NO:4) encoded by the nucleic acid sequence in FIG. 2A. Amino acids 1-21 correspond to the leader sequences; 22-345 correspond to the HA1 domain; 346-565 correspond to the HA2 domain; 529-551 correspond to the transmembrane domain; and 552-565 correspond to the cytoplasmic domain.

FIG. 3A is schematic diagram depicting various influenza H1 HA polypeptides encoded by nucleic acid constructs described herein. "Wt" refers to a leader sequence that is naturally associated with the influenza polypeptide. "tPA" refers to the tissue plasminogen leader sequence. "dTM" refers to a polypeptide lacks a transmembrane domain and cytoplasmic domain.

FIG. 3B is a schematic diagram depicting various influenza H3 HA polypeptides described herein. "dTM" refers to a polypeptide lacks a transmembrane domain and cytoplasmic.

FIGS. 5A-5I are graphs depicting the results of assays to determine reactivity of antisera from rabbits immunized with various codon optimized DNA vectors encoding influenza HA polypeptides. Rabbits were immunized with the following vectors: H1-wt.HA0, H1-tPA.HA0, H1-tPA.HA0.dTM (FIG. 5A); H1-tPA.HA1, H1-tPA.HA2, H1-tPA.HA2.dTM (FIG. 5B); H3-wt.HA0, H3-tPA.HA0, H3-tPA.HA0.dTM (FIG. 5D); H3-tPA.HA1, H3-tPA.HA2, H3-tPA.HA2.dTM (FIG. 5E); H1+H3 tPA.HA0.dTM, H1+H3 tPA.HA1, or empty vector (FIGS. 5C and 5F). Levels of HA-specific antibodies in sera at each time point were examined by ELISA and are plotted in the graphs. FIG. 5G depicts HA-specific IgG titers in sera from rabbits immunized with each of the various H1 HA vectors, or empty vector. The sera analyzed in these assays were collected two weeks after the fourth immunization. FIG. 5H depicts HA-specific IgG titers in sera from rabbits immunized with each of the various H3 HA vectors, or empty vector. The sera analyzed in these assays were collected two weeks after the fourth immunization. FIG. 5I depicts HA-specific IgG titers in sera from rabbits immunized with the following two combinations of vectors: H1-tPA.HA0.dTM and H3-tPA.HA0dTM; H1-wt.HA0 and H3-tPA.HA0.dTM.

FIG. 6A is a representation of a codon optimized influenza A N2 NA nucleic acid sequence (SEQ ID NO:5).

FIG. 6B is a representation of the influenza A N2 NA amino acid sequence (SEQ ID NO:6) encoded by the nucleic acid sequence in FIG. 6A.

FIG. 7 is a schematic diagram depicting various influenza ion channel M2 polypeptides described herein.

FIG. 8 is a schematic diagram depicting various influenza NA and NA/M2 fusion polypeptide vaccines described herein.

FIG. 9 is a representation of a sequence encoding H1 HA from influenza A New Caledonia/20/99 (SEQ ID NO:7; See also Genbank® Acc. No. AJ344014.1; GI No. 19849783).

FIG. 10 is a representation of an influenza viral sequence encoding an influenza H3 HA polypeptide from Influenza A/Panama/2007/99(H3N2)(SEQ ID NO:8).

FIG. 11 is a representation of a sequence encoding NA from Influenza A/Panama/2007/99(H3N2)(SEQ ID NO:9; See GenBank® Acc. No. AJ457937.1; GI No. 22859354).

FIG. 13C is a graph depicting the results of assays to determine reactivity of antisera from mice immunized with codon-optimized H1 HA DNA (H1-HA.opt), non-codon-optimized H1 HA DNA (H1-HA.wt), or an empty DNA vector. HA-specific IgG titers in sera collected two weeks after the fourth immunization were measured.

Antigens with Amino Acid Substitutions

Figure 4A:
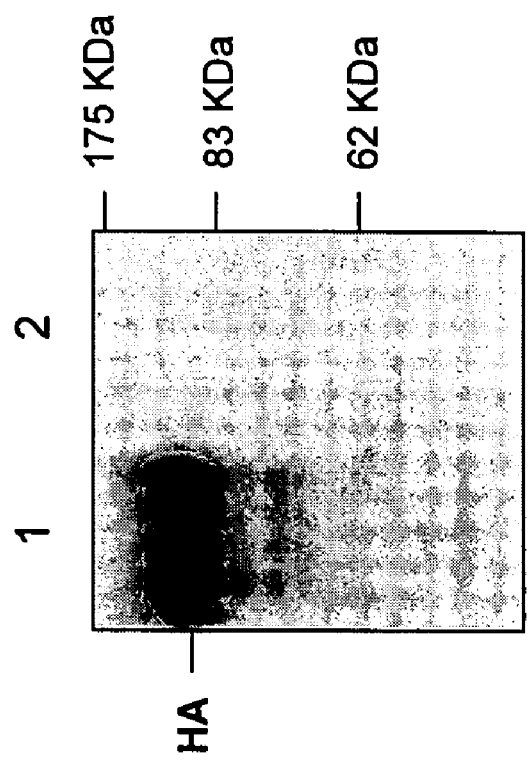
FIG. 4A is a representation of SDS-PAGE and Western blot analysis of H1 HA polypeptides expressed in 293T cells (lane 1) as compared to a negative control (vector only; lane 2).
Figure 4B:
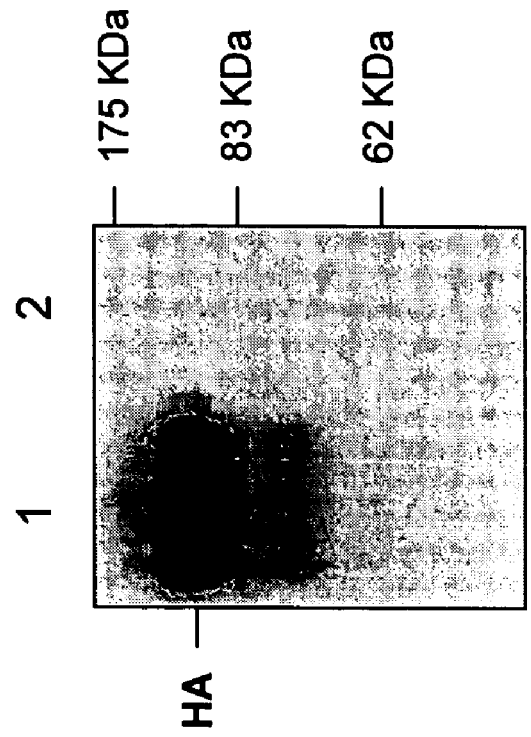
FIG. 4B is a representation of SDS-PAGE and Western blot analysis of H1 HA polypeptides expressed in 293T cells (lane 1) as compared to a negative control (vector only; lane 2).
Figure 5A:
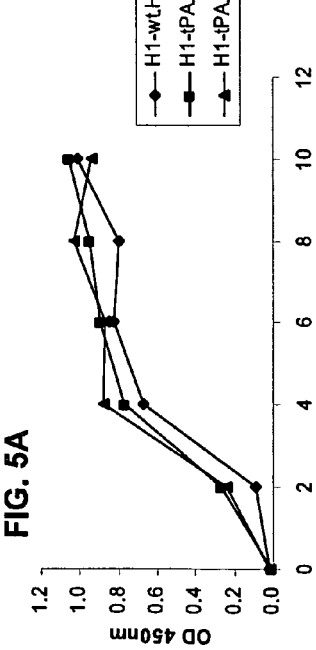
Figure 5B:
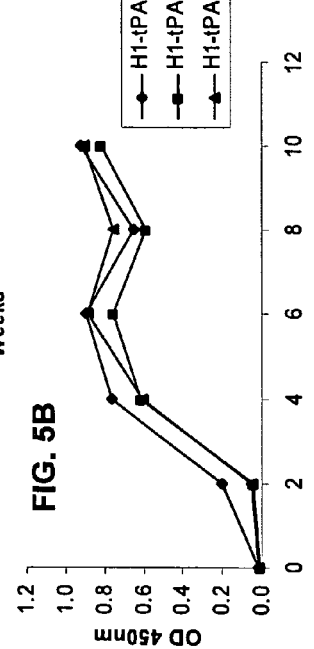
Figure 5C:
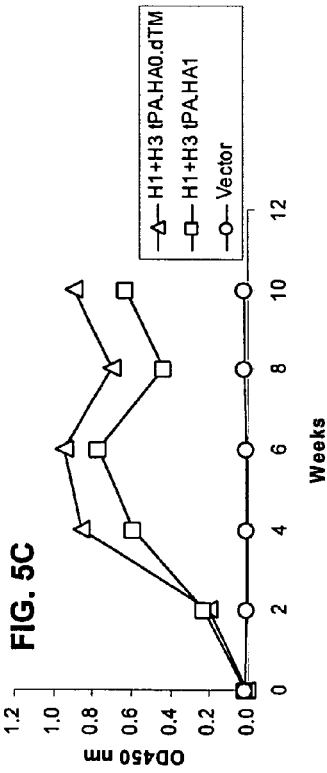
Figure 5G:
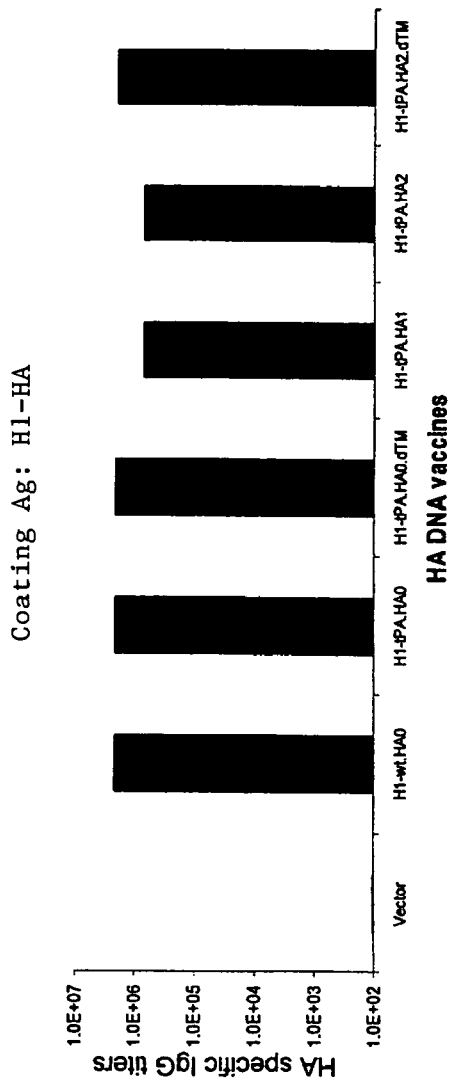
Figure 5H:
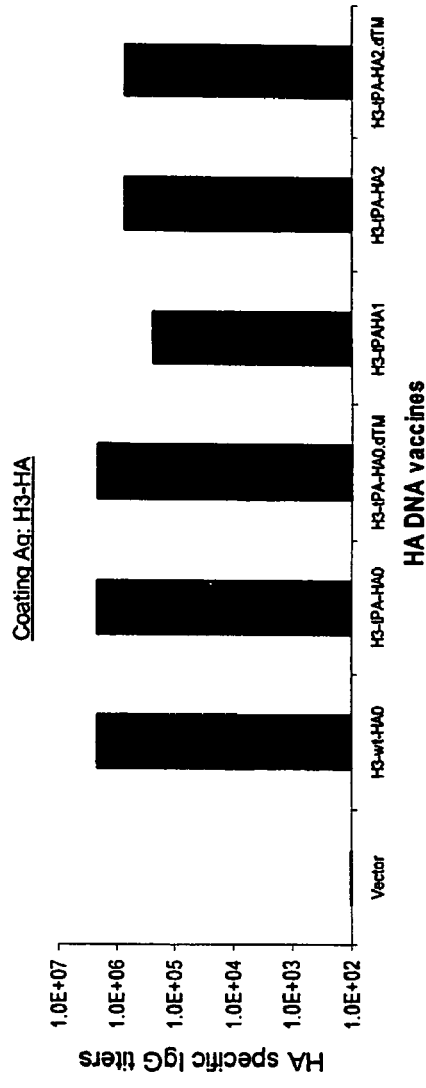
Figure 5I:
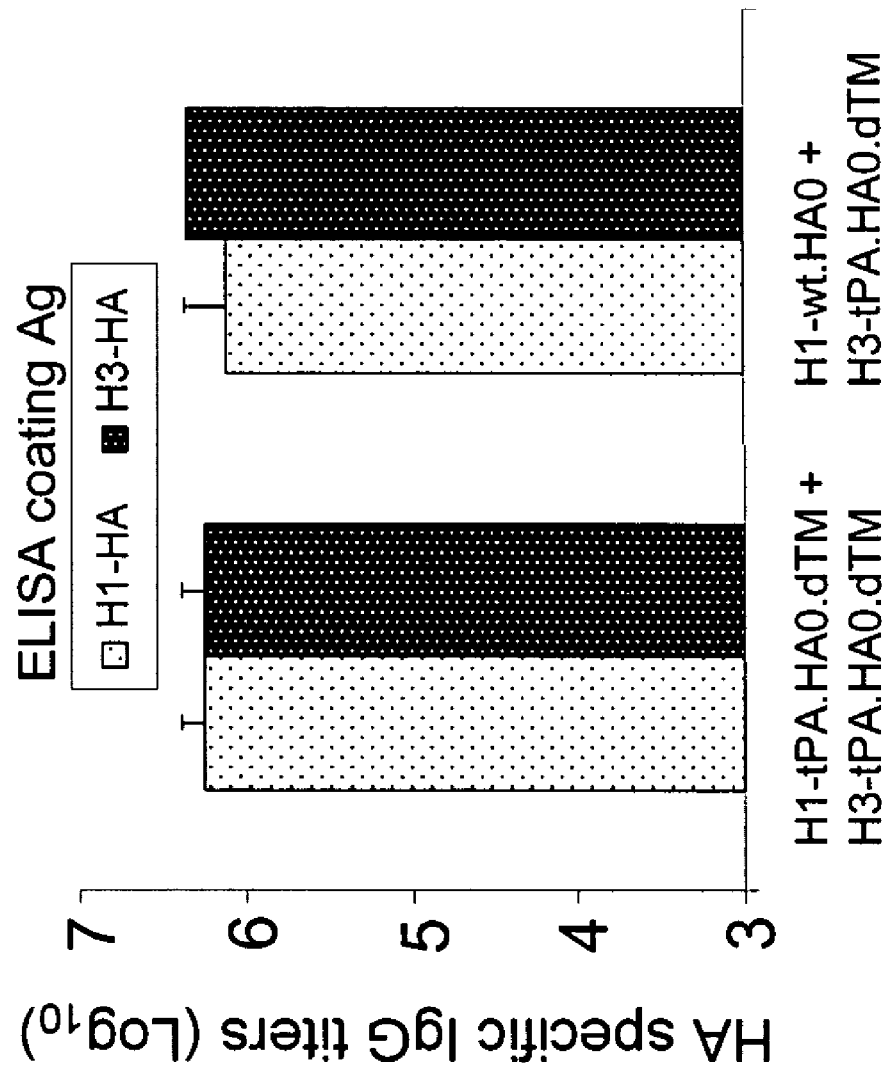

It is understood that the influenza polypeptides and fragments thereof described herein may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie et al., (1990) *Science*, 247:1306-1310. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a polypeptide, such as a binding agent, e.g., an antibody, without substantially altering a biological activity, whereas an "essential" amino acid residue results in such a change.

Construction of Optimized Sequences

Viral proteins and proteins that are naturally expressed at low levels can provide challenges for efficient expression by recombinant means. In addition, viral proteins often display a codon usage that is inefficiently translated in a host cell (e.g., a mammalian or avian host cell). Alteration of the codons native to the viral sequence can facilitate more robust expression of these proteins. Codon preferences for abundantly expressed proteins have been determined in a number of species, and can provide guidelines for codon substitution. Synthesis of codon-optimized sequences can be achieved by substitution of viral codons in cloned sequences, e.g., by site-directed mutagenesis, or by construction of oligonucleotides corresponding to the optimized sequence by chemical synthesis. See, e.g., Mirzabekov et al., *J. Biol. Chem.*, 274 (40):28745-50, 1999.

The optimization should also include consideration of other factors such as the efficiency with which the sequence can be synthesized in vitro (e.g., as oligonucleotide segments) and the presence of other features that affect expression of the nucleic acid in a cell. For example, sequences that result in RNAs predicted to have a high degree of secondary structure should be avoided. AT- and GC-rich sequences that interfere with DNA synthesis should also be avoided. Other motifs that can be detrimental to expression include internal TATA boxes, chi-sites, ribosomal entry sites, procarya inhibitory motifs, cryptic splice donor and acceptor sites, and branch points. These features can be identified manually or by computer software and they can be excluded from the optimized sequences.

An influenza polypeptide (e.g., HA or NA) or antigenic fragment thereof encoded by a codon-optimized nucleic acid is any polypeptide sharing an epitope with a naturally occurring influenza polypeptide, e.g., an HA or NA polypeptide. The influenza polypeptides provided herein can differ from a wild type sequence by additions or substitutions within the amino acid sequence, and may preserve a biological function of the influenza polypeptide (e.g., receptor binding). Amino acid substitutions may be made on the basis of similarity in polarity, charge, solubility, hydrophobicity, hydrophilicity, and/or the amphipathic nature of the residues involved.

Nonpolar (hydrophobic) amino acids include alanine, leucine, isoleucine, valine, proline, phenylalanine, tryptophan, and methionine. Polar neutral amino acids include glycine, serine, threonine, cysteine, tyrosine, asparagine, and glutamine. Positively charged (basic) amino acids include arginine, lysine, and histidine. Negatively charged (acidic) amino acids include aspartic acid and glutamic acid.

Alteration of residues are preferably conservative alterations, e.g., a basic amino acid is replaced by a different basic amino acid, as described herein.

Nucleic Acids, Vectors, and Host Cells

Isolated nucleic acid, vector, and host cell compositions that can be used, e.g., for recombinant expression of the optimized influenza nucleic acid sequences (e.g., HA, NA, or M2) and for vaccines are provided herein.

Prokaryotic or eukaryotic host cells may be used for expression of the influenza polypeptides. The terms "host cell" and "recombinant host cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic cells, e.g., bacterial cells such as *E. coli*, or eukaryotic cells, e.g., insect cells, yeast, avian cells (e.g., chicken cells, duck cells), or mammalian cells (e.g., cultured cell or a cell line, e.g., a primate cell such as a Vero cell, or a human cell). Other suitable host cells are known to those skilled in the art.

The recombinant expression vectors provided herein can be designed for expression of the influenza polypeptides (e.g., HA, NA), anti-influenza antibodies, or antigen-binding fragments thereof, in prokaryotic or eukaryotic cells. For example, new polypeptides described herein can be expressed in *E. coli*, insect cells (e.g., using baculovirus expression vectors), yeast cells, avian cells, or mammalian cells. Suitable host cells are discussed further in Goeddel, *Gene Expression Technology: Methods in Enzymology* 185, Academic Press, San Diego, Calif., 1990. Alternatively, the recombinant expression vector can be transcribed and translated in vitro, for example using T7 promoter regulatory sequences and T7 polymerase.

Expression of proteins in prokaryotes is often carried out in *E. coli* with vectors containing constitutive or inducible promoters directing the expression of either fusion or non-fusion proteins. Fusion vectors add a number of amino acids to protein or antibody encoded therein, usually to the constant region of a recombinant antibody.

A nucleic acid that is codon-optimized for expression in mammalian cells can be expressed in mammalian cells using a mammalian expression vector. Examples of mammalian expression vectors include pCDM8 (Seed, B. *Nature* 329: 840, 1987) and pMT2PC (Kaufman et al., *EMBO J.* 6:187-195, 1987). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see, e.g., Chapters 16 and 17 of Sambrook, J., Fritsh, E. F., and Maniatis, T.,

*Molecular Cloning: A Laboratory Manual.*, 2nd ed., Cold Spring Harbor Laboratory, Cold Spring Harbor Laboratory Press, Cold Spring Harbor, N.Y., 1989.

In one embodiment, the recombinant expression vector (e.g., recombinant mammalian expression vector) is capable of directing expression of the nucleic acid preferentially in a particular cell type (e.g., in which tissue-specific regulatory elements are used to express the nucleic acid). Tissue-specific regulatory elements are known in the art. Non-limiting examples of suitable tissue-specific promoters include the albumin promoter (liver-specific; Pinkert et al., *Genes Dev.*, 1:268-277, 1987), lymphoid-specific promoters (Calame and Eaton, *Adv. Immunol.*, 43:235-275, 1988), in particular promoters of T cell receptors (Winoto and Baltimore, *EMBO J.*, 8:729-733, 1989) and immunoglobulins (Banerji et al., *Cell*, 33:729-740, 1983; Queen and Baltimore, *Cell*, 33:741-748, 1983), neuron-specific promoters (e.g., the neurofilament promoter; Byrne and Ruddle, *Proc. Natl. Acad. Sci., USA* 86:5473-5477, 1989), pancreas-specific promoters (Edlund et al., *Science,* 230:912-916, 1985), and mammary gland-specific promoters (e.g., milk whey promoter; U.S. Pat. No. 4,873,316 and European Application Publication No. 264, 166). Developmentally-regulated promoters are also encompassed, for example the murine hox promoters (Kessel and Gruss, *Science,* 249:374-379, 1990 and the α-fetoprotein promoter (Campes and Tilghman, *Genes Dev.*, 3:537-546, 1989).

In addition to the coding sequences, the new recombinant expression vectors described herein carry regulatory sequences that are operatively linked and control the expression of the genes in a host cell.

As used herein, the term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the first antibody.

Calculations of "homology" or "identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In different embodiments, the length of a reference sequence aligned for comparison purposes is at least 60%, e.g., at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences are accomplished using a mathematical algorithm. The percent homology between two amino acid sequences is determined using the Needleman and Wunsch, *J. Mol. Biol.*, 48:444-453, 1970, algorithm which has been incorporated into the GAP program in the GCG software package, using a Blossum 62 scoring matrix with a gap penalty of 12, a gap extend penalty of 4, and a frameshift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology,* John Wiley & Sons, N.Y., 1989, 6.3.1-6.3.6, which is incorporated herein by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

Nucleic Acid Vaccines

The nucleic acids useful for inducing an immune response include at least three components: (1) a nucleic acid sequence that begins with a start codon and encodes an influenza polypeptide or antigenic fragment thereof, (2) a transcriptional promoter operatively linked to the sequence encoding the influenza polypeptide or antigenic fragment thereof, and (3) a mammalian polyadenylation signal operably linked to the coding sequence to terminate transcription driven by the promoter. In this context, a "mammalian" promoter or polyadenylation signal is not necessarily a nucleic acid sequence derived from a mammal. For example, it is known that mammalian promoters and polyadenylation signals can be derived from viruses.

The nucleic acid vector can optionally include additional sequences such as enhancer elements, splicing signals, termination and polyadenylation signals, viral replicons, and bacterial plasmid sequences. Such vectors can be produced by methods known in the art. For example, a nucleic acid encoding the desired influenza polypeptide can be inserted into various commercially available expression vectors. See, e.g., Invitrogen Catalog, 1998. In addition, vectors specifically constructed for nucleic acid vaccines are described in Yasutomi et al., *J. Virol.,* 70:678-681, 1996.

Administration of Nucleic Acids

The new nucleic acids described herein can be administered to an individual, e.g., naked, in combination with a carrier, or in combination with a substance that promotes nucleic acid uptake or recruits immune system cells to the site of the inoculation. For example, nucleic acids encapsulated in microparticles have been shown to promote expression of rotaviral proteins from nucleic acid vectors in vivo (U.S. Pat. No. 5,620,896).

A mammal can be inoculated with nucleic acid through any parenteral route, e.g., intravenous, intraperitoneal, intradermal, subcutaneous, intrapulmonary, or intramuscular routes. The new nucleic acid compositions can also be administered orally, by particle bombardment using a gene gun, or by other needle-free delivery systems. Muscle is a useful tissue for the delivery of nucleic acids encoding influenza polypeptides because mammals have a proportionately large muscle mass which is conveniently accessed by direct injection through the skin. A comparatively large dose of nucleic acid can be deposited into muscle by multiple and/or repetitive injections. Multiple injections can be performed over extended periods of time.

Conventional particle bombardment can be used to deliver nucleic acids that express influenza polypeptides into skin or onto mucosal surfaces, e.g., using commercial devices. For example, the Accell II® (PowderJect® Vaccines, Inc., Middleton, Wis.) particle bombardment device, one of several commercially available "gene guns," can be employed to deliver nucleic acid-coated gold beads. A Helios Gene Gun® (Bio-Rad) can also be used to administer the DNA particles. Information on particle bombardment devices and methods can be found in sources including the following: Yang et al., *Proc. Natl. Acad. Sci. USA,* 87:9568, 1990; Yang, *CRC Crit. Rev. Biotechnol.,* 12:335, 1992; Richmond et al., *Virology,* 230:265-274, 1997; Mustafa et al., *Virology,* 229:269-278, 1997; Livingston et al., *Infect. Immun.,* 66:322-329, 1998; and Cheng et al., *Proc. Natl. Acad. Sci. USA,* 90:4455, 1993.

In some embodiments, an individual is inoculated by a mucosal route. The codon-optimized nucleic acids or compositions can be administered to a mucosal surface by a variety of methods including nucleic acid-containing nose-drops, inhalants, suppositories, or microspheres. Alternatively, nucleic acid vectors containing the codon-optimized nucleic acids can be encapsulated in poly(lactide-co-glycolide) (PLG) microparticles by a solvent extraction technique, such as the ones described in Jones et al., *Infect. Immun.,* 64:489, 1996; and Jones et al., *Vaccine,* 15:814, 1997. For example, the nucleic acids can be emulsified with PLG dissolved in dichloromethane, and this water-in-oil emulsion is emulsified with aqueous polyvinyl alcohol (an emulsion stabilizer) to form a (water-in-oil)-in-water double emulsion. This double emulsion is added to a large quantity of water to dissipate the dichloromethane, which results in the microdroplets hardening to form microparticles. These microdroplets or microparticles are harvested by centrifugation, washed several times to remove the polyvinyl alcohol and residual solvent, and finally lyophilized. The microparticles containing nucleic acid have a mean diameter of 0.5 μm.

To test for nucleic acid content, the microparticles are dissolved in 0.1 M NaOH at 100° C. for 10 minutes. The $A_{260}$ is measured, and the amount of nucleic acid calculated from a standard curve. Incorporation of nucleic acid into microparticles is in the range of 1.76 g to 2.7 g nucleic acid per milligram PLG. Microparticles containing about 1 to 100 μg of nucleic acid are suspended in about 0.1 to 1 ml of 0.1 M sodium bicarbonate, pH 8.5, and orally administered to mice or humans.

Regardless of the route of administration, an adjuvant can be administered before, during, or after administration of the codon-optimized nucleic acid encoding an influenza polypeptide. An adjuvant can increase the uptake of the nucleic acid into the cells, increase the expression of the polypeptide from the nucleic acid within the cell, induce antigen presenting cells to infiltrate the region of tissue where the polypeptide is being expressed, or increase the antigen-specific response provided by lymphocytes.

Evaluating Vaccine Efficacy

Before administering the nucleic acids, polypeptides, and/or antibodies described herein to humans, efficacy testing can be conducted using animals. In an example of efficacy testing, mice are vaccinated by intramuscular injection. After the initial vaccination or after optional booster vaccinations, the mice (and negative controls) are monitored for indications of vaccine-induced, influenza-specific immune responses. Methods of measuring immune responses are described in Townsend et al., *J. Virol.,* 71:3365-3374, 1997; Kuhober et al., *J. Immunol.,* 156: 3687-3695, 1996; Kuhrober et al., *Int. Immunol.,* 9:1203-1212, 1997; Geissler et al., *Gastroenterology,* 112:1307-1320, 1997; and Sallberg et al., *J. Virol.,* 71:5295-5303, 1997.

Anti-influenza serum antibody levels in vaccinated animals can be determined by known methods. The concentrations of antibodies can be standardized against a readily available reference standard. The functional activity of antibodies can be measured, e.g., using hemagglutination inhibition assays and/or virus neutralization assays (described in Example 5, below).

Cytotoxicity assays can be performed as follows. Spleen cells from immunized mice are suspended in complete MEM with 10% fetal calf serum and $5\times10^{-5}$ M 2-mercapto-ethanol. Cytotoxic effector lymphocyte populations are harvested after 5 days of culture, and a 5-hour $^{51}Cr$ release assay is performed in a 96-well round-bottom plate using target cells. The effector to target cell ratio is varied. Percent lysis is defined as (experimental release minus spontaneous release)/(maximum release minus spontaneous release)×100.

Antibodies

This invention also provides, inter alia, antibodies, or antigen-binding fragments thereof, to influenza polypeptides, e.g., HA, NA, M2, and/or antigenic fragments of the polypeptides, e.g., portions of the polypeptides that lack transmembrane domains.

As used herein, "specific binding" or "specifically binds to" refer to the ability of an antibody to: (1) bind to an influenza polypeptide as shown by a specific biochemical analysis, such as a specific band in a Western Blot analysis, or (2) bind to an influenza polypeptide with a reactivity that is at least two-fold greater than its reactivity for binding to an antigen (e.g., BSA, casein) other than an influenza polypeptide.

As used herein, the term "antibody" refers to a protein including at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" (CDR), interspersed with regions that are more conserved, termed "framework regions" (FR). Each VH and VL is composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

As used herein, "isotype" refers to the antibody class (e.g., IgM or IgG1) that is encoded by heavy chain constant region genes.

The term "antigen-binding fragment" of an antibody (or simply "antibody portion," or "fragment"), as used herein, refers to a portion of an antibody that specifically binds to an influenza polypeptide (e.g., HA or NA), e.g., a molecule in which one or more immunoglobulin chains is not full length, but which still specifically binds to an influenza polypeptide. Examples of antigen-binding fragments include: (i) a Fab fragment, a monovalent fragment consisting of the VL, VH, CL, and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated complementarity determining region (CDR) having sufficient framework to specifically bind to, e.g., an antigen binding portion of a variable region. An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al., *Science,* 242:423-426, 1988; and Huston et al., *Proc. Natl. Acad. Sci. USA,* 85:5879-5883, 1988). Such single chain antibodies are also encompassed within the term "antigen-binding fragment" of an antibody. These antibody fragments are obtained using conventional techniques known to those with skill in the art, and are screened for utility in the same manner as are intact antibodies.

The term "monospecific antibody" refers to an antibody that displays a single binding specificity and affinity for a particular target, e.g., an epitope. This term includes a "monoclonal antibody" or "monoclonal antibody composition," which as used herein refer to a preparation of antibodies or fragments thereof of single molecular composition.

The term "polyclonal antibody" refers to an antibody preparation, either as animal or human sera or as prepared by in vitro production, which can bind to more than one epitope on one antigen or multiple epitopes on more than one antigen.

The term "recombinant" antibody, as used herein, refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, in vitro generated (e.g., by phage display) antibodies, and may optionally include constant regions derived from human germline immunoglobulin sequences.

Many types of anti-influenza antibodies, or antigen-binding fragments thereof, are useful in the methods described herein. The antibodies can be of the various isotypes, including: IgG (e.g., IgG1, IgG2, IgG3, IgG4), IgM, IgA1, IgA2, IgD, or IgE. Preferably, the antibody is an IgG isotype, e.g., IgG1. The antibody molecules can be full-length (e.g., an IgG1 or IgG4 antibody) or can include only an antigen-binding fragment (e.g., a Fab, F(ab')$_2$, Fv or a single chain Fv fragment). These include monoclonal antibodies, recombinant antibodies, chimeric antibodies, human antibodies, and humanized antibodies, as well as antigen-binding fragments of the foregoing.

Monoclonal antibodies can be used in the new methods described herein. Monoclonal antibodies can be produced by a variety of techniques, including conventional monoclonal antibody methodology, e.g., the standard somatic cell hybridization technique of Kohler and Milstein, *Nature* 256:495, 1975. Polyclonal antibodies can be produced by immunization of animal or human subjects. The advantages of polyclonal antibodies include the broad antigen specificity against a particular pathogen. See generally, Harlow, E. and Lane, D. (1988) *Antibodies: A Laboratory Manual,* Cold Spring Harbor Laboratory Press, Cold Spring Harbor, N.Y.

Useful immunogens for uses described herein include the influenza polypeptides described herein, e.g., influenza polypeptides expressed from codon-optimized nucleic acid sequences.

Anti-influenza antibodies or fragments thereof useful in methods described herein can also be recombinant antibodies produced by host cells transformed with DNA encoding immunoglobulin light and heavy chains of a desired antibody. Recombinant antibodies may be produced by known genetic engineering techniques. For example, recombinant antibodies can be produced by cloning a nucleotide sequence, e.g., a cDNA or genomic DNA, encoding the immunoglobulin light and heavy chains of the desired antibody. The nucleotide sequences encoding those polypeptides are then inserted into expression vectors so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is useful because such cells are more likely than prokaryotic cells to assemble and secrete a properly folded and immunologically active antibody. However, any antibody produced that is inactive due to improper folding may be renatured according to well known methods (Kim and Baldwin, "Specific Intermediates in the Folding Reactions of Small Proteins and the Mechanism of Protein Folding," *Ann. Rev. Biochem.,* 51, pp. 459-89 (1982)). It is possible that the host cells will produce portions of intact antibodies, such as light chain dimers or heavy chain dimers, which also are antibody homologs.

It will be understood that variations on the above procedure are useful. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for binding, e.g., the constant region may be modified by, for example, deleting specific amino acids. The molecules expressed from such truncated DNA molecules are useful in the methods described herein. In addition, bifunctional antibodies may be produced in which one heavy and one light chain are anti-influenza antibody and the other heavy and light chain are specific for an antigen other than the influenza polypeptide, or another epitope of the same influenza, or of another influenza polypeptide.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., *Science,* 240:1041-1043, 1988; Liu et al., *Proc. Natl. Acad. Sci.,* 84:3439-3443, 1987; Liu et al., *J. Immunol.,* 139:3521-3526, 1987; Sun et al., *Proc. Natl. Acad. Sci.,* 84:214-218, 1987; Nishimura et al., *Canc. Res.,* 47:999-1005, 1987; Wood et al., *Nature,* 314:446-449, 1985; and Shaw et al., *J. Natl Cancer Inst.,* 80:1553-1559, 1988).

An antibody or an immunoglobulin chain can be humanized by methods known in the art. For example, once murine antibodies are obtained, variable regions can be sequenced. The location of the CDRs and framework residues can be determined (see, Kabat et al., *Sequences of Proteins of Immunological Interest, Fifth Edition,* U.S. Department of Health and Human Services, NIH Publication No. 91-3242, 1991, and Chothia, C. et al., *J. Mol. Biol.,* 196:901-917, 1987, which are incorporated herein by reference). The light and heavy chain variable regions can, optionally, be ligated to corresponding constant regions.

Murine antibodies can be sequenced using art-recognized techniques. Humanized or CDR-grafted antibody molecules or immunoglobulins can be produced by CDR-grafting or CDR substitution, wherein one, two, or all CDRs of an immunoglobulin chain can be replaced. See e.g., U.S. Pat. No. 5,225,539; Jones et al., *Nature,* 321:552-525, 1986; Verhoeyan et al., *Science,* 239:1534, 1988; Beidler et al., *J. Immunol.,* 141:4053-4060, 1988; and Winter, U.S. Pat. No. 5,225,539, the contents of all of which are hereby expressly incorporated by reference.

Winter describes a CDR-grafting method that may be used to prepare the humanized anti-influenza antibodies (Winter U.S. Pat. No. 5,225,539), the contents of which is expressly incorporated by reference. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, *Science,* 229:1202-1207, 1985, by Oi et al., *BioTechniques,* 4:214, 1986, and by Queen et al., U.S. Pat. Nos. 5,585,089; 5,693,761; and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

Also included herein are humanized antibodies in which specific amino acids have been substituted, deleted, or added. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089 (e.g., columns 12-16), the contents of which are hereby incorporated by reference. The acceptor framework can be a mature human antibody framework sequence or a consensus sequence.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence. Other techniques for humanizing antibodies are described in Padlan et al. EP 519596 A1, published on Dec. 23, 1992.

Also provided herein are antibodies that are produced in mice that bear transgenes encoding one or more fragments of an immunoglobulin heavy or light chain. See, e.g., U.S. Patent Publication No. 20030138421. Also provided are antibodies that are fully human (100% human protein sequences) produced in transgenic mice in which mouse antibody gene expression is suppressed and effectively replaced with human antibody gene expression (such mice are available, e.g., from Medarex, Princeton, N.J.). See, e.g., U.S. Patent Publication No. 20030031667.

An antibody, or antigen-binding fragment thereof, can be derivatized or linked to another functional molecule (e.g., another peptide or protein). For example, a protein or antibody can be functionally linked (by chemical coupling, genetic fusion, noncovalent association or otherwise) to one or more other molecular entities, such as another antibody, a detectable agent, a cytotoxic agent, a pharmaceutical agent, and/or a protein or peptide that can mediate association with another molecule (such as a streptavidin core region or a polyhistidine tag).

One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which a protein can be derivatized (or labeled) to include fluorescent compounds, various enzymes, prosthetic groups, luminescent materials, bioluminescent materials, and radioactive materials. Exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, β-galactosidase, acetylcholinesterase, glucose oxidase and the like. When a protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A protein can also be derivatized with a prosthetic group (e.g., streptavidin/biotin and avidin/biotin). For example, an antibody can be derivatized with biotin, and detected through indirect measurement of avidin or streptavidin binding.

Labeled proteins and antibodies can be used, for example, diagnostically and/or experimentally in a number of contexts, including (i) to isolate a predetermined antigen by standard techniques, such as affinity chromatography or immunoprecipitation; (ii) to detect a predetermined antigen (e.g., an influenza virion, e.g., in a cellular lysate or a serum sample) in order to evaluate the abundance and pattern of expression of the protein; and (iii) to monitor protein levels in tissue as part of a clinical testing procedure, e.g., to determine the efficacy of a given treatment regimen.

An anti-influenza antibody or antigen-binding fragment thereof may be conjugated to another molecular entity, typically a label or a therapeutic (e.g., a cytotoxic or cytostatic) agent or moiety.

Radioactive isotopes can be used in diagnostic or therapeutic applications. Radioactive isotopes that can be coupled to proteins and antibodies include, but are not limited to α-, β-, or γ-emitters, or β- and γ-emitters.

Pharmaceutical Compositions

In another aspect, compositions, e.g., pharmaceutically acceptable compositions, are provided which include a polypeptide or antibody molecule described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion).

The compositions may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Useful compositions are in the form of injectable or infusible solutions. A useful mode of administration is parenteral (e.g., intravenous, subcutaneous, intraperitoneal, intramuscular). For example, the protein or antibody can be administered by intravenous infusion or injection. In another embodiment, the protein or antibody is administered by intramuscular or subcutaneous injection.

Compositions for administration to animals and humans typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., codon-optimized nucleic acid or polypeptide) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The compositions can be administered by a variety of methods known in the art, although for many therapeutic and prophylactic applications. As will be appreciated by the skilled artisan, the route and/or mode of administration will vary depending upon the desired results.

In certain embodiments, a composition (e.g., codon-optimized nucleic acid composition) may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation. Therapeutic compositions can be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of a polypeptide or antigenic fragment thereof is 0.1-100 mg/kg, e.g., 1-10 mg/kg. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. The exact dosage can vary depending on the route of administration. For intramuscular injection, the dose range can be 100 μg (microgram) to 10 mg (milligram) per injection. Multiple injections may be needed.

Suitable doses of nucleic acid compositions for humans can range from 1 μg/kg to 1 mg/kg of total nucleic acid, e.g., from 5 μg/kg-500 mg/kg of total DNA, 10 μg/kg-250 μg/kg of total DNA, or 10 μg/kg-170 μg/kg of total DNA. In one embodiment, a human subject (18-50 years of age, 45-75 kg) is administered 1 mg-10 mg of DNA. "Total DNA" and "total nucleic acid" refers to a pool of nucleic acids encoding distinct antigens. For example, a dose of 50 mg of total DNA encoding five different influenza HA antigens can have 1 mg of each antigen. DNA vaccines can be administered multiple times, e.g., between two-six times, e.g., three times. In an exemplary method, 100 μg of a DNA composition is administered to a human subject at 0, 4, and 12 weeks (100 μg per administration).

The pharmaceutical compositions described herein can include a therapeutically effective amount or a prophylactically effective amount of a nucleic acid, polypeptide, antibody, or antibody portion. A therapeutically effective amount of a codon-optimized nucleic acid vaccine, polypeptide, or antibody or antibody fragment varies according to factors such as the disease state, age, sex, and weight of the individual, and the ability of the composition to elicit a desired response in the individual. A therapeutically effective amount is also one in which any toxic or detrimental effects of the pharmaceutical composition is outweighed by the therapeutically beneficial effects. The ability of a compound to inhibit a measurable parameter can be evaluated in an animal model system predictive of efficacy in the target subject (e.g., a human subject). Alternatively, this property of a composition can be evaluated by examining the ability of the compound to modulate, such modulation in vitro by assays known to the skilled practitioner.

A "prophylactically effective amount" refers to an amount effective, at dosages and for periods of time necessary, to achieve the desired prophylactic result, i.e., protective immunity against a subsequent challenge by the influenza virus. Typically, since a prophylactic dose is used in subjects prior to or at an earlier stage of disease, the prophylactically effective amount will be less than the therapeutically effective amount. Also provided herein are kits including one or more of a codon-optimized nucleic acid encoding an influenza polypeptide, the polypeptide encoded by the nucleic acid, and/or an anti-influenza antibody or antigen-binding fragment thereof. The kits can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the composition for administration; pharmaceutically acceptable carriers; and devices or other materials for administration to a subject.

Instructions for use can include instructions for diagnostic applications of the nucleic acid sequence, polypeptides, or antibodies (or antigen-binding fragment thereof) to detect influenza, in vitro, e.g., in a sample, e.g., a biopsy or cells from a patient, or in vivo. The instructions can include instructions for therapeutic or prophylactic application including suggested dosages and/or modes of administration, e.g., in a patient at risk for or suffering from a symptom of influenza.

The kit can further contain at least one additional reagent, such as a diagnostic or therapeutic agent, e.g., one or more additional codon-optimized nucleic acid encoding and influenza polypeptide, and/or an antiviral agent in one or more separate pharmaceutical preparations.

Therapeutic Uses

The new nucleic acid vaccines, polypeptides, and antibodies described herein have in vitro and in vivo diagnostic, therapeutic, and prophylactic utilities. For example, the nucleic acid vaccines can be administered to cells in culture, e.g., in vitro or ex vivo, or in a subject, e.g., in vivo, to treat, prevent, and/or diagnose influenza.

As used herein, the term "subject" is intended to include humans and non-human animals. The term "non-human animals" includes all vertebrates, e.g., mammals and non-mammals, such as non-human primates, pigs, chickens and other birds, mice, dogs, cats, cows, and horses.

Methods of administering nucleic acid vaccines, polypeptide, and antibody compositions are described above. Suitable dosages of the molecules used will depend on the age and weight of the subject and the particular drug used. The nucleic acid vaccines can be used to prevent an influenza infection by inducing a protective immunity in the inoculated subject, or to treat an existing influenza infection if improved immune responses can be useful in controlling the viral infection. The antibody molecules can be used to reduce or alleviate an acute influenza infection.

In other embodiments, immunogenic compositions and vaccines that contain an immunogenically effective amount of an influenza polypeptide, or antigenic fragments thereof, are provided. Immunogenic epitopes in a polypeptide sequence can be identified according to methods known in the art, and proteins, or fragments containing those epitopes can be delivered by various means, in a vaccine composition.

The polypeptide and nucleic acid compositions described herein can be used in combination with agents used for inducing immune responses to influenza in humans, such as trivalent inactivated influenza vaccines (e.g., trivalent vaccines that include H1N1, H3N2, and influenza B strains). Other compositions suitable for use in combination with the novel nucleic acid and polypeptide compositions described herein include live influenza vaccines such as cold-adapted influenza vaccines (see, e.g., Wareing and Tannock, *Vaccine,* 19(25-26):3320-3330, 2001) and vaccines generated by reverse genetics (see, e.g., Hoffmann et al., *Vaccine,* 20(25-26):3165-3170, 2002). These compositions can be administered simultaneously with, before, or after a composition described herein.

Suitable compositions can include, for example, lipopeptides (e.g., Vitiello et al., *J. Clin. Invest.,* 95:341, 1995), peptide compositions encapsulated in poly(DL-lactide-co-glycolide) ("PLG") microspheres (see, e.g., Eldridge et al., *Molec. Immunol.,* 28:287-94, 1991; Alonso et al., *Vaccine,* 12:299-306, 1994; Jones et al., *Vaccine,* 13:675-81, 1995), peptide compositions contained in immune stimulating complexes (ISCOMS) (see, e.g., Takahashi et al., *Nature,* 344: 873-75, 1990; Hu et al., *Clin. Exp. Immunol.,* 113:235-43, 1998), and multiple antigen peptide systems (MAPs) (see, e.g., Tam, *Proc. Natl. Acad. Sci. U.S.A.,* 85:5409-13, 1988; Tam, *J. Immunol. Methods,* 196:17-32, 1996). Toxin-targeted delivery technologies, also known as receptor-mediated targeting, such as those of Avant Immunotherapeutics, Inc. (Needham, Mass.) can also be used.

Useful carriers that can be used with immunogenic compositions and vaccines are well known, and include, for example, thyroglobulin, albumins such as human serum albumin, tetanus toxoid, polyamino acids such as poly L-lysine, poly L-glutamic acid, influenza, hepatitis B virus core protein, and the like. The compositions and vaccines can contain a physiologically tolerable (i.e., acceptable) diluent such as water, or saline, typically phosphate buffered saline. The compositions and vaccines also typically include an adjuvant. Adjuvants such as incomplete Freund's adjuvant, aluminum phosphate, aluminum hydroxide, or alum are examples of materials well known in the art. Additionally, CTL responses can be primed by conjugating influenza polypeptides (or fragments, derivatives or analogs thereof) to lipids, such as tripalmitoyl-S-glycerylcysteinyl-seryl-serine ($P_3CSS$).

Immunization with a composition or vaccine containing a protein composition, e.g., via injection, aerosol, oral, transdermal, transmucosal, intrapleural, intrathecal, or other suitable routes, induces the immune system of the host to respond to the composition or vaccine by producing large amounts of CTLs, and/or antibodies specific for the desired antigen. Consequently, the host typically becomes at least partially immune to later infection (e.g., with influenza), or at least partially resistant to developing an ongoing chronic infection, or derives at least some therapeutic benefit. In other words, the subject is protected against subsequent infection by the influenza virus.

EXAMPLES

The invention is further described in the following examples, which do not limit the scope of the invention described in the claims.

Example 1

Construction of Codon-Optimized Sequences Encoding Influenza HA and NA Polypeptides To generate DNA for efficient expression of influenza HA and NA polypeptides and various fragments of these polypeptides, codon-optimized nucleic acids were constructed. These codon-optimized nucleic acids were designed to express polypeptides with amino acid sequences identical, or nearly identical, to sequences encoded by the native influenza polypeptide but with codons known to be efficiently translated in mammalian host cells. Substitution of viral codons for mammalian codons can facilitate high levels of expression of viral proteins in recombinant systems.

The codon usage of HA-encoding sequences from influenza A H1N1 and H3N2 strains and the NA-encoding sequence from H3N2 was analyzed by the MacVector software (V. 7.2, Accelrys, San Diego, Calif.) against that of the *Homo sapiens* genome. Sequences were generated in which the codons in the influenza sequences that are less optimal for mammalian expression were changed to the codons more preferred in mammalian systems. The sequences were also designed to avoid unwanted RNA motifs, such as internal TATA-boxes, chi-sites, ribosomal entry sites, AT-rich or GC-rich sequence stretches, repeat sequences, sequences likely to encode RNA with secondary structures, (cryptic) splice donor and acceptor sites, or branch points.

The codon-optimized nucleic acids encoding H1 HA, H3 HA, and N2 NA polypeptides were chemically synthesized. The codon-optimized nucleic acid sequence and amino acid sequence encoded by the nucleic acids are shown in FIGS. 1A, 1B, 2A, 2B, 6A, and 6B, respectively. The viral sequence from which SEQ ID NO:1 was derived is shown in FIG. 9 as SEQ ID NO:7. The viral sequence from which SEQ ID NO:3 was derived is shown in FIG. 10 as SEQ ID NO:8. The viral sequence from which SEQ ID NO:5 was derived is shown in FIG. 11 as SEQ ID NO:9.

We constructed expression vectors that encode six different forms of the HA polypeptides, shown schematically in FIGS. 3A and 3B. These forms were: a wild type, full length HA sequence containing a sequence encoding the native HA leader peptide (wt.HA0); a full length HA sequence encoding a tPA leader peptide (tPA.HA0); an HA sequence encoding the external portion of HA with a tPA leader peptide (tPA.HA0.dTM); a sequence encoding the HA1 domain of HA with a tPA leader peptide (tPA.HA1); a sequence encoding the HA2 domain of HA with a tPA leader peptide (tPA.HA2);.and a sequence encoding the HA2 domain of the HA polypeptide lacking the transmembrane region, also with a tPA leader peptide (tPA.HA2.dTM).

We designed expression vectors that encode four different forms of NA polypeptides, shown schematically in FIG. 8. These forms are a wild type, full length NA sequence containing a sequence encoding the native NA leader peptide (wt.NA); a full length NA sequence encoding a tPA leader peptide (tPA.NA); an NA sequence encoding the external portion of NA with a tPA leader peptide (tPA.NA.dTM); a sequence encoding a fusion protein of M2 polypeptide extracellular domain (M2-ex) and the external portion of NA with a tPA leader peptide (tPA.M2-NA.dTM).

The sequences described above were subcloned into DNA vaccine vector pSW3891 (Wang et al., *Journal of Virology,* 79:1906-1910, 2005) which is a modified form of the pJW4303 vector (Lu et al., *Methods in Molecular Medicine,* 29:355-74, 1998). The pSW3891 vector contains a cytomegalovirus immediate early promoter (CMV-IE) with its downstream Intron A sequence for initiating transcription of eukaryotic gene inserts and a bovine growth hormone (BGH) poly-adenylation signal for termination of transcription. For certain constructs, a human tissue plasminogen activator (tPA) leader sequence was included to direct expression of secreted proteins. The vector also contains the ColE1 origin of replication for prokaryotic replication and the kanamycin resistance gene for selective growth in antibiotic containing media.

Each individual DNA plasmid was confirmed by DNA sequencing before large amounts of DNA plasmids were prepared from *Escherichia coli* (HB101 strain) with a Mega purification kit (Qiagen, Valencia, Calif.) for both in vitro transfection and in vivo animal immunization studies.

Example 2

Expression of Codon-Optimized HA Polypeptides In Vitro and Immunogenicity In Vivo HA expression in vitro. Cells (293T) were transfected with the codon-optimized wt.HA0 vector encoding full-length, wild-type H1 HA. Expression of the HA antigen was evaluated by Western blotting. HA was detected using a commercial anti-HA monoclonal antibody. As shown in FIGS. 4A and 4B, the HA antigen was expressed in 293T cells. Cells transfected with empty vectors (as a negative control) did not express HA antigen.

Immunization. NZW Rabbits (female, ~2 kg each) were purchased from Millbrook Farms (Millbrook, Mass.) and housed in the Department of Animal Medicine at the University of Massachusetts Medical School (UMMS) in accordance with IACUC approved protocols. The animals were immunized with a Helios gene gun (Bio-Rad, Hercules, Calif.) at the shaved abdominal skin as previously reported (Wang et al., Methods Mol. Biol., 245:185-96, 2004). A total of 36 μg of plasmid DNA was administrated to each individual rabbit for each immunization at 0, 2, 4, and 8 weeks. Serum samples were taken at 0, 2, 4, 6, 8, and 10 weeks after each immunization for analyses of HA-specific antibody responses. Animals were immunized with wt.HA0, tPA.HA0, tPA.HA0.dTM, tPA.HA1, tPA.HA2, tPA.HA2.dTM vectors encoding H1 or H3 subtype HA antigens. A subset of animals were immunized with both H1 tPA.HA0 and H3 tPA.HA0 or both H1 tPA.HA1 and H3 tPA.HA1 vectors.

ELISA to Determine Anti-HA Antibody Responses. ELISA assays were conducted to measure the anti-HA antibody responses in immunized rabbits. The ELISA plates were coated with 100 or 200 μl/well of either H1 or H3 HA antigen (1 μg/ml in PBS at pH 7.2) from the supernatant of 293T cells transiently transfected with tPA.HA0.dTM overnight at 4° C. Plates were washed five times with PBS containing 0.1% Triton X-100 and blocked with 200 μl/well of blocking buffer (5% non-fat dry milk, 4% whey, 0.5% Tween-20 in PBS at pH 7.2) for 1 hour. After five washes, 100 µl of rabbit serum diluted 1:5000 in Whey dilution buffer (4% Whey, 0.5% Tween-20 in PBS) was added in duplicate wells and incubated for 1 hour at room temperature. After another set of washes, the plates were incubated for 1 hour at room temperature with 100 µl of biotinylated anti-rabbit IgG (Vector Laboratories) diluted at 1:1000 in Whey dilution buffer. Then 100 µl of horseradish peroxidase-conjugated streptavidin (Vector Laboratories) diluted at 1:2000 in Whey buffer was added to each well and incubated for 1 hour. After the final wash, the plates were developed with 3,3',5,5' Tetramethybenzidine solution at 100 µl per well (Sigma, St. Louis, Mo.) for 3.5 minutes. The reactions were stopped by adding 25 µl of 2 M $H_2SO_4$, and the plates were read at OD 450 nm. The results of these assays are depicted in FIGS. 5A-5I.

All of the HA-encoding DNA constructs tested induced antibodies to HA antigens in the rabbits. Thus, the codon-optimized sequences were expressed in the animals and the polypeptides they expressed were immunogenic. Rabbits immunized with constructs encoding both H1 and H3 HA antigens (FIGS. 5C, 5F, and 5I) mounted responses to both H1 and H3 HA antigens, i.e., it does not appear that immunization with two DNAs compromised the response to either one. The ability to induce a robust response to antigens of multiple subtypes simultaneously can convey broader protection than would result from vaccination with a monovalent construct.

Example 3

Construction of Influenza M2 DNA Vectors

The influenza M2 polypeptide contains approximately 23 amino acids in the extracellular domain. This region of the polypeptide is a potential target of protective antibodies reported recently (Neirynck et al., *Nature Medicine*, 5:1157-1163, 1999; Fan, et al., *Vaccine*, 22:2993-3003, 2005). However, short synthetic peptides, instead of recombinant protein, have been used in previous studies due to the difficulty of expressing M2 protein. We can enhance immunogenicity of M2 by expressing multiple copies of the extracellular domain of M2 as a fusion, as shown schematically in FIG. 7. DNA expressing these M2 fusions, or the polypeptides expressed by the DNA, can be administered to animals to induce immune responses against this antigen. DNA expressing M2 fused to a second type of influenza antigen (e.g., HA or NA, or a fragment thereof), or the fusion polypeptides themselves, can also be used to induce immune responses in animals. See, e.g., the tPA.M2-NA.dTM construct depicted in FIG. 8.

Example 4

Figure 12:
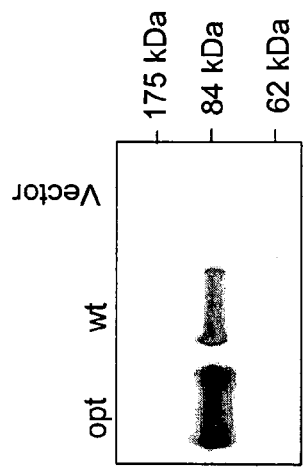
FIG. 12 is a representation of SDS-PAGE and Western blot analysis of H1 HA polypeptides expressed in mammalian cells transfected with a codon-optimized nucleic acid sequence ("opt"; lane 1), a wild-type nucleic acid sequence ("wt"; lane 2) or vector only (lane 3).

Comparison of Immune Responses Induced by Codon-Optimized and Wild-Type Influenza Nucleic Acid Sequences HA expression in vitro. To compare expression of codon-optimized and non-codon-optimized (wild-type) sequences in vitro, mammalian cells were transfected with either a codon-optimized nucleic acid encoding H1 HA or a wild-type nucleic acid encoding H1 HA. Expression of the HA antigen was evaluated by Western blotting. HA was detected using a commercial anti-HA monoclonal antibody. As shown in FIG. 12, the H1 HA antigen was expressed more robustly in cells transfected with the codon-optimized sequence as compared to cells transfected with the wild-type sequence. Cells transfected with empty vectors (as a negative control) did not express HA antigen.

Figure 13A:
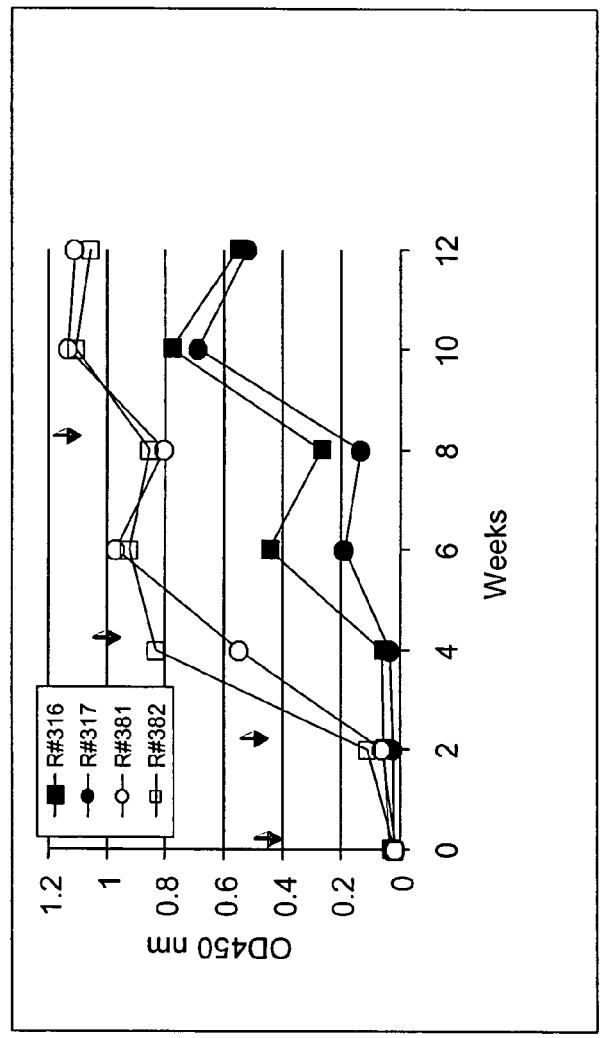
FIG. 13A is a graph depicting the results of assays to determine reactivity of antisera from rabbits immunized with codon-optimized or non-codon-optimized (wild-type) influenza protein sequences. Levels of HA-specific antibodies in sera at each time point were examined by ELISA and are plotted in the graph. Rabbits #316 and #317 (filled-in symbols) received wild-type DNA encoding H1 HA. Rabbits #381 and #382 (open symbols) received codon-optimized DNA encoding H1 HA.
Figure 13B:
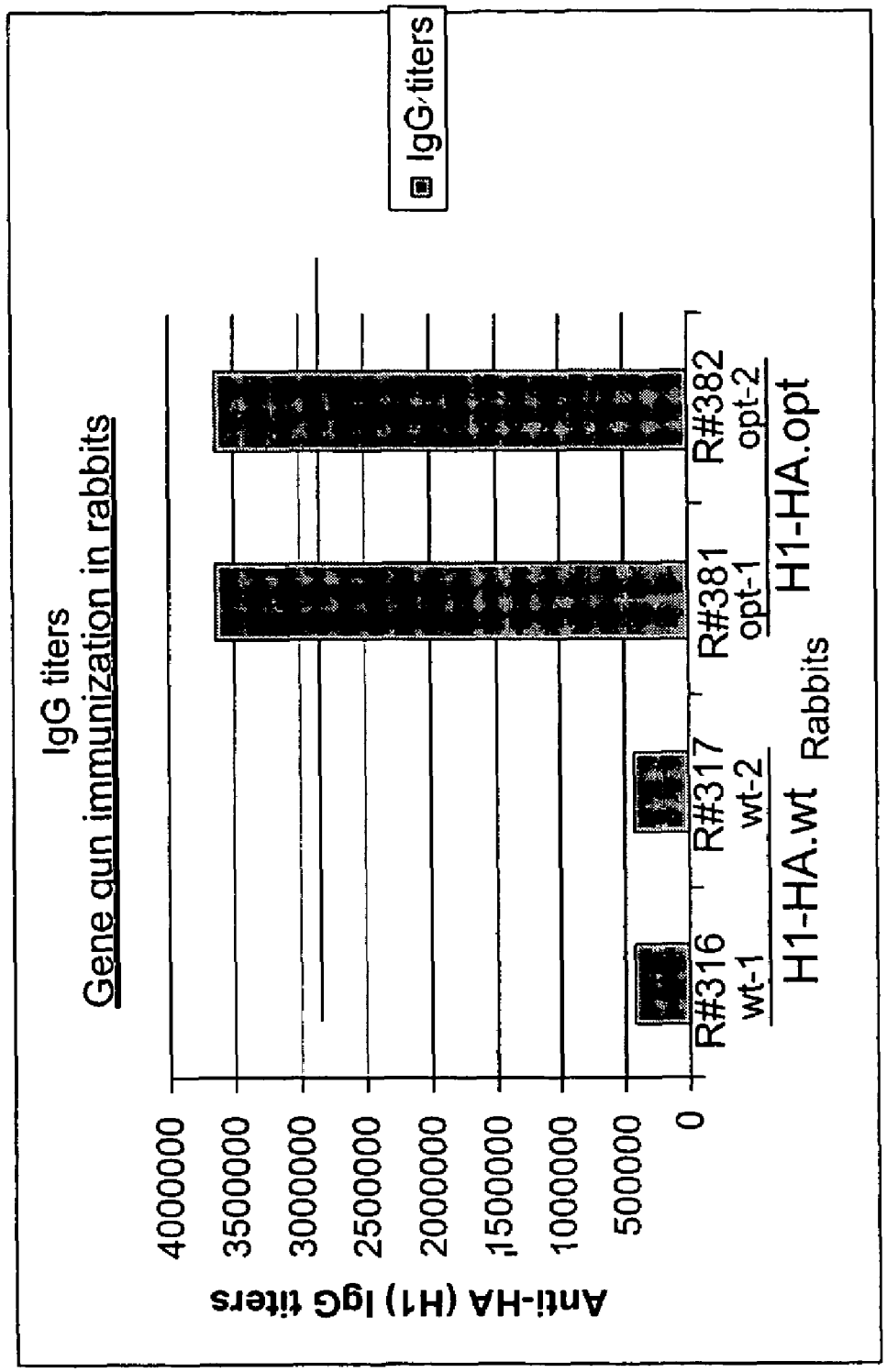
FIG. 13B is a graph depicting the results of assays to determine reactivity of antisera from rabbits immunized with codon-optimized or non-codon-optimized (wild-type) influenza protein sequences. HA-specific IgG titers were detected two weeks after the fourth immunization with codon-optimized or wild-type DNA encoding H1 HA. Rabbits #316 and #317 received wild-type DNA encoding H1 HA. Rabbits #381 and #382 received codon-optimized DNA encoding H1 HA.

Antibody responses induced by codon-optimized and wild-type nucleic acid sequences. Rabbits were immunized with codon-optimized or wild-type H1 HA nucleic acid sequences and ELISA assays were conducted with sera from immunized rabbits. Immunization and ELISA protocols are described above in Example 2. Animals were immunized at 0, 2, 4, and 8 weeks. Sera samples collected at 0, 2, 4, 6, 8, 10, and 12 weeks were tested by ELISA at 1:5000 serum dilutions. The results of this experiment are depicted in FIG. 13A. Rabbits R#316 and R#317 were immunized with the wild-type H1 HA DNA while rabbits R#381 and R#382 received the codon-optimized H1 HA DNA. The antibody titers in animals immunized with the codon-optimized H1 HA DNA were higher than titers in animals immunized with wild-type H1 HA DNA at all time points examined after week 0. FIG. 13B depicts anti-HA IgG titers in sera from the animals collected two weeks after the fourth immunization. These data show that codon-optimized DNA induced anti-HA titers much higher than titers induced by wild-type influenza DNA sequences, with average titers of approximately 3,500,000 and 500,000, respectively, indicating that the codon-optimized DNAs are expressed at a higher level than non-codon-optimized DNAs.

A similar immunization experiment was performed in mice. Mice were immunized four times with codon-optimized H1 HA DNA or wild-type H1 HA DNA. A set of mice was also immunized with empty vector as a control. Sera collected two weeks after the fourth immunization were tested for anti-HA IgG titers. Group mean titers are plotted in FIG. 13C. The results depicted in FIG. 13C show that codon-optimized DNA induced anti-HA titers much higher than titers induced by wild-type influenza DNA sequences, with average titers of approximately 2,000,000 and 200,000, respectively. Sera from mice immunized with empty vector did not contain any detectable HA-reactive IgG.

Example 5

Sera from Animals Immunized with Codon-Optimized DNA Mediate Hemagglutinin Inhibition and Virus Neutralization Hemagglutination Inhibition. Sera from animals immunized with various codon-optimized DNAs encoding H1 HA or H3 HA were tested in standard hemagglutination inhibition assays (HAI or HI) in the presence of the A/NewCaledonia/20/99 (H1N1) influenza strain and the A/Panama/2007/99 (H3N2) influenza strain.

Hemagglutination inhibition assays were performed with sera that had been pre-treated with bacterial neuraminidase/Receptor Destroying Enzyme (RDE) to remove nonspecific inhibitors of virus hemagglutination. Briefly, 25 µl of a preparation of influenza virus (hemagglutination titer=8) was mixed with 25 µl of 2-fold dilutions of the specific RDE-treated serum in PBS in V-bottom 96-well plates. After 30 minutes incubation at 4 degrees, 50 µl of 0.5% chicken red blood cells were added to the mixtures. The plates were incubated at 4 degrees until hemagglutination occurred in non-serum containing control wells. The H1 titer is defined as the highest dilution of serum that inhibits hemagglutination.

Figure 14A:
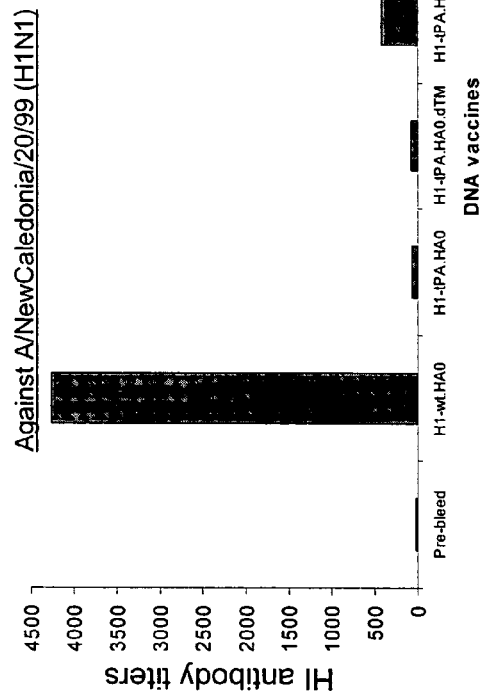
FIG. 14A is a graph depicting the results of assays to determine the titers of hemagglutination-inhibiting antibodies against the H1N1 influenza virus A/NewCaledonia/20/99 strain in sera from animals immunized with the following codon-optimized H1 HA DNA vectors: H1-wt.HA0, H1-tPA.HA0, H1-tPA.HA0.dTM; H1-tPA.HA1, H1-tPA.HA2, H1-tPA.HA2.dTM. A sera sample from animals that were not yet immunized was also tested (pre-bleed).
Figure 14B:
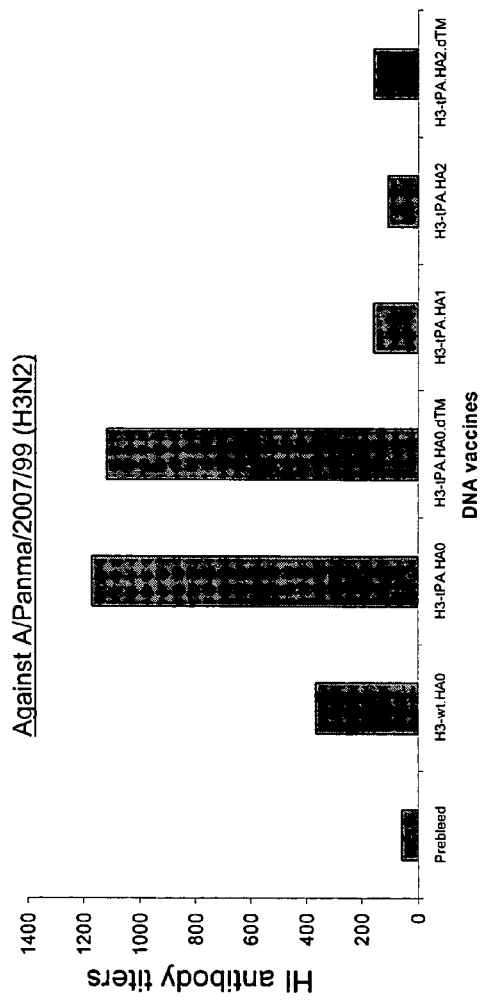
FIG. 14B is a graph depicting the results of assays to determine the titers of hemagglutination-inhibiting antibodies against the H3N2 influenza virus A/Panama/2007/99 strain in sera from animals immunized with the following codon-optimized H3 HA DNA vectors: H3-wt.HA0, H3-tPA.HA0, H3-tPA.HA0.dTM, H3-tPA.HA1, H3-tPA.HA2, and H3-tPA-HA2.dTM. A sera sample from animals that were not yet immunized was also tested (pre-bleed).

The HI antibody titers are depicted in FIGS. 14A and 14B. Sera from animals immunized with a codon-optimized DNA encoding a full-length H1 HA, wt.HA0, exhibited the highest level of hemagglutination activity towards the H1N1 A/New-Caledonia/20/99 strain (FIG. 14A).

Sera from animals immunized with codon-optimized DNA encoding full-length H3 HA with a tPA leader sequence (tPA-HA0) and DNA encoding H3 HA lacking the transmembrane region (tPA.HA0.dTM) exhibited the highest levels of hemagglutination activity (FIG. 14B). Activity was also observed in sera from animals immunized with DNA encoding full length H3 HA with a wild-type leader sequence (wt.HA0) and with DNA encoding HA1, HA2, and partial HA2 domains of H3 HA (tPA.HA1, tPA.HA2, and tPA.HA2.dTM, respectively).

Neutralizing antibody responses. Neutralizing antibody responses induced by various codon-optimized DNAs encoding H1 HA or H3 HA were determined. The assays were performed using viruses which were able to infect cells and express green fluorescent protein (GFP), but which do not propagate (replication is restricted to a single cycle). To generate the replication-restricted virus for these assays, 293 cells were transfected with 8 viral RNA expression plasmids and with 5 viral protein expression plasmids. The HA viral RNA expression plasmids were replaced by a GFP viral RNA expression plasmid that includes the 3' and 5' HA-specific regions required for the replication, transcription and packaging of this RNA into an influenza virus, as previously described. Transfected 293 cells were co-cultured with an MDCK cell line expressing the desired influenza virus HA protein. Viruses in which the HA gene is replaced by the GFP gene were obtained and propagated in the HA-expressing MDCK cell line. In the presence of HA neutralizing antibodies, infection and GFP expression by these viruses is prevented.

Figure 15A:
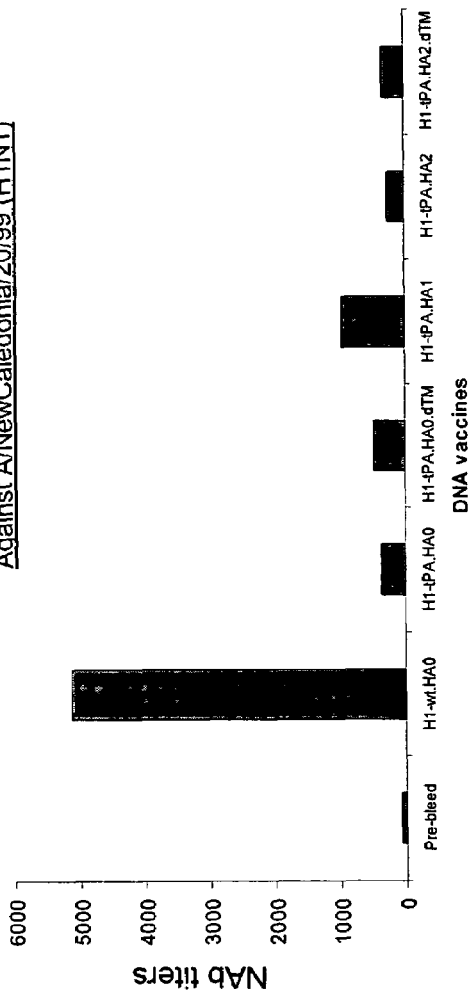
FIG. 15A is a graph depicting the results of assays to determine the titers of neutralizing antibodies against the H1N1 influenza virus A/NewCa (Wang et al., *J. Virol.*, 67(9):5585-5594, 1993). Mutations in M2, typically in the transmembrane region, cause resistance to amantidine.
Figure 15B:
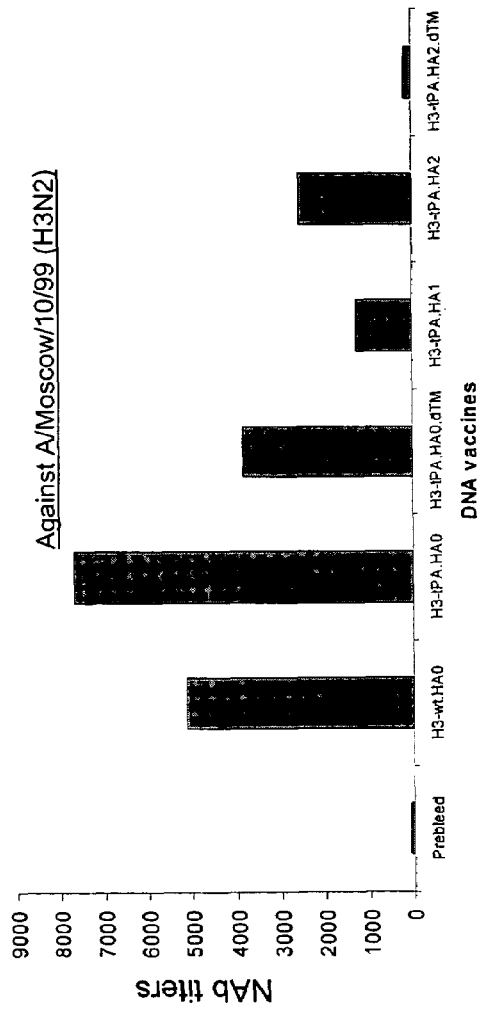

Sera from animals immunized with various codon-optimized H1 HA vectors were tested against H1N1 influenza virus A/NewCaledonia/20/99 (FIG. 15A). The highest levels of neutralizing antibody titers were detected in sera from animals immunized with a vector encoding the full-length H1 HA, wt.HA0.

Sera from animals immunized with various codon-optimized H3 HA vectors were tested against H3N2 influenza virus A/Moscow/10/99. Sera from animals immunized with DNA encoding full-length H3 HA with a tPA leader sequence, tPA.HA0, exhibited the highest levels of neutralizing activity. Activity was observed in sera from animals immunized with wt.HA0, tPA.HA0.dTM, tPA.HA1, and tPA.HA2 vectors.

In summary, these data show that different vectors induce different levels of functional antibody responses although they induce similar levels of binding antibody responses when measured by ELISA.

Figures 16A, 16B:
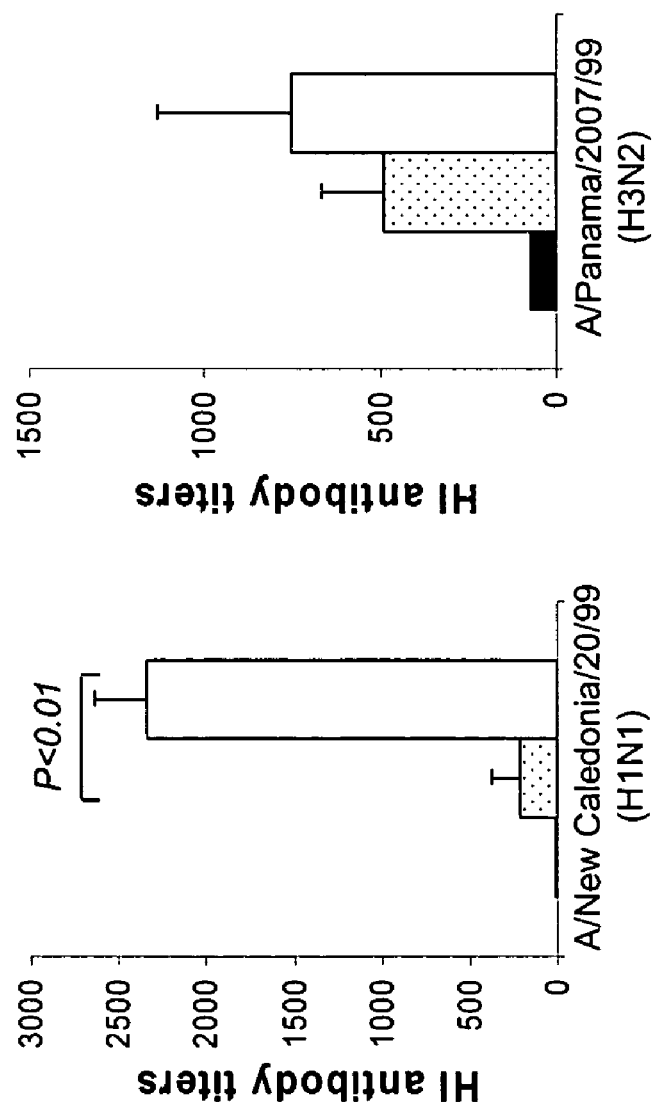

Hemagglutination inhibition and bivalent immunization. Hemagglutination inhibition by sera from animals immunized with two different codon-optimized DNAs encoding H1 HA or H3 HA were determined. Sera from animals immunized with the combinations of codon-optimized H1 HA vectors were tested against H1N1 influenza virus A/NewCaledonia/20/99 and H3N2 influenza virus A/Panama/2007/99 (FIGS. 16A and 16B). Animals were immunized with either H1-tPA.HA0.dTM and H3-tPA.HA0.dTM; or with H1-wt.HA0 and H3-tPA.HA0.dTM. Sera from animals immunized with the latter combination showed the highest levels of hemagglutination inhibition activity against both virus strains. Activity was more modest in sera from animals immunized with the former combination, and higher levels of activity were seen against the H3N2 Panama strain.

Figures 16C, 16D:
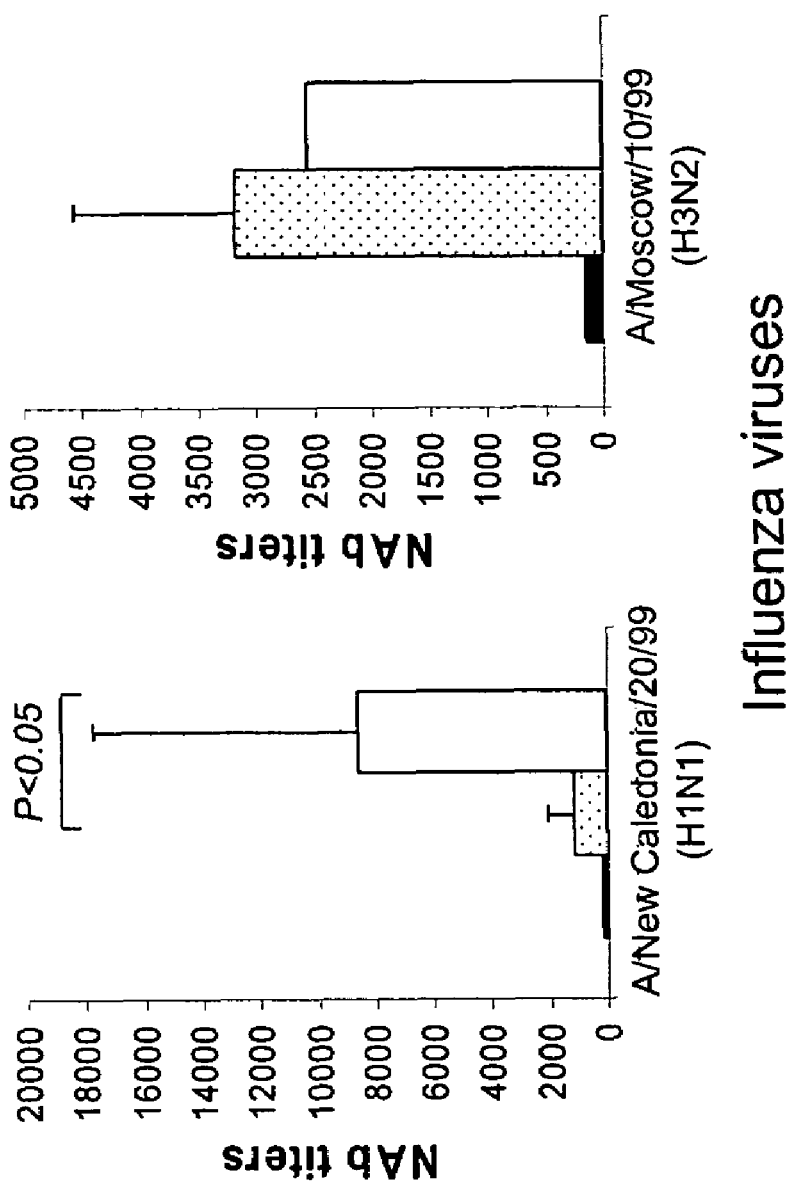

Neutralization and bivalent immunization. Neutralizing activity induced by bivalent immunization was also examined. The same bivalent combinations described in the previous paragraph were tested. In these experiments, neutralizing activity to H1N1 influenza virus A/NewCaledonia/20/99 and H3N2 influenza virus A/Moscow/10/99 was examined. Sera from animals immunized with the first combination (H1-tPA.HA0.dTM+H3-tPA.HA0.dTM) exhibited low titers to the H1N1 New Caledonia strain yet exhibited high titers to the H3N2 Moscow strain (FIGS. 16C and 16D). Sera from the second combination (H1-wt.HA0+H3-tPA.HA0.dTM) exhibited high levels of neutralizing titers against both strains.

In summary, H1 HA constructs encoding full-length H1 HA (as opposed to a form lacking the transmembrane region) induced higher levels of protective antibodies against H1 strains in both monovalent and bivalent immunization regimens. In contrast, constructs encoding both full-length H3 HA and forms lacking the transmembrane region were effective in inducing protective antibodies.

Example 6

Immunization with Multiple Agents

The codon-optimized nucleic acids described herein (and other compositions described herein) may be used in combination with other agents that induce immune responses to influenza antigens. In the following experiments, codon-optimized DNAs encoding H1 HA and H3 HA (H1-HA0.wt+H3-HA0.dTM; 250 micrograms/dose of each DNA) were administered to rabbits at week 0 followed by a boost with Fluzone® (Aventis Pasteur), an influenza vaccine prepared from inactivated influenza virus, at week 4. Another set of rabbits was administered Fluzone® alone, at weeks 0 and 4. Fluzone® (0.25 ml/dose) was administered by intramuscular injection. Sera collected at week 8 from both sets of animals were examined.

Figure 17B:
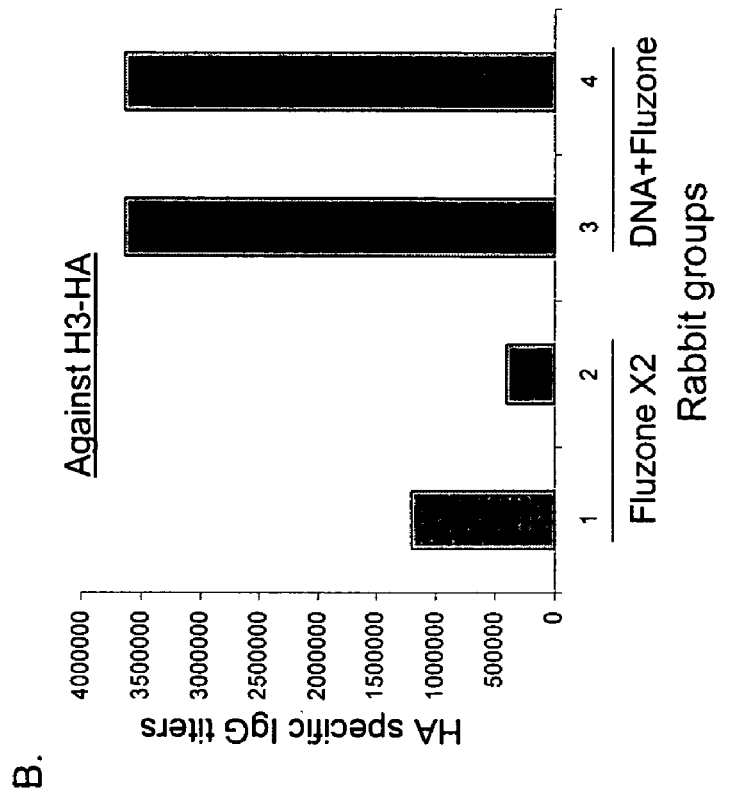
Figure 17A:
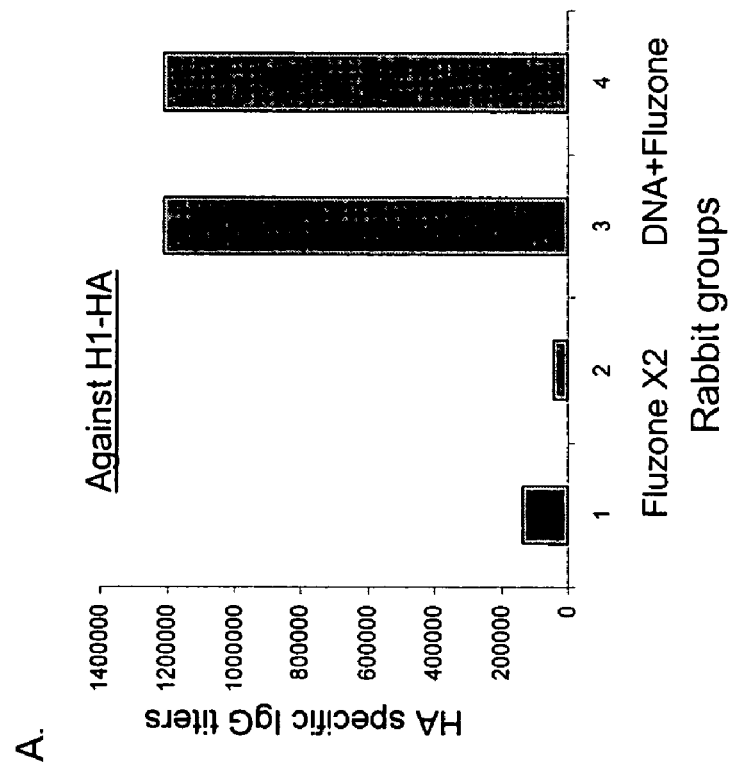

HA-specific IgG responses were determined by ELISA. The results are depicted in FIGS. 17A and 17B. Sera from animals administered Fluzone® alone contained IgG titers of less than 200,000 to H1 HA and titers of less than 1,250,000 to H3 HA. In contrast, sera from animals administered the bivalent H1 HA, H3 HA prime and Fluzone® boost exhibited very high titers of HA-specific IgG. Titers to H1 HA were approximately 1,200,000. Titers to H3 HA were approximately 3,500,000. These results show that the DNA prime, Fluzone® boost protocol was much more effective in inducing HA-specific antibodies than the use of Fluzone® alone.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method for inducing an immune response to one or more influenza polypeptides in a subject, the method comprising:
   administering to the subject a composition comprising (a) a nucleic acid molecule comprising a sequence encoding an influenza type hemagglutinin (HA) polypeptide of an H1 subtype or an antigenic fragment thereof, wherein the sequence is at least 95% identical to SEQ ID NO:1, or comprises at least 30 contiguous nucleotides that are identical to 30 contiguous nucleotides of SEQ ID NO:1, and wherein the sequence is codon-optimized for expression in a mammalian cell; (b) a mammalian promoter operably linked to the nucleic acid molecule, wherein the promoter directs transcription of mRNA encoding the influenza polypeptide; and (c) a mammalian polyadenylation signal operably linked to the nucleic acid molecule, wherein the composition is administered in an amount sufficient for the sequence to express the influenza polypeptide at a level sufficient to induce an immune response in the subject.

2. The method of claim 1, further comprising administering to the subject a second composition comprising an influenza polypeptide.

3. The method of claim 2, wherein the second composition comprises influenza virions.

4. The method of claim 1, wherein the sequence is SEQ ID NO:1.

5. The method of claim 1, wherein the antigenic fragment comprises an external domain of the HA polypeptide.

6. The method of claim 1, wherein the antigenic fragment comprises an HA1 domain of the HA polypeptide.

7. The method of claim 1, wherein the antigenic fragment comprises an HA2 domain of the HA polypeptide.

8. The method of claim 1, wherein the composition further comprises a second nucleic acid molecule comprising a second sequence encoding an influenza type HA polypeptide of an H3 subtype or an antigenic fragment thereof, wherein the second sequence is codon-optimized for expression in a mammalian cell.

9. The method of claim 8, wherein the second sequence is at least 95% identical to SEQ ID NO:3, or comprises at least 30 contiguous nucleotides that are identical to 30 contiguous nucleotides of SEQ ID NO:3.

10. A method for inducing an immune response to one or more influenza polypeptides in a subject, the method comprising:

administering to the subject a composition comprising (a) a nucleic acid molecule comprising a sequence encoding an influenza type hemagglutinin (HA) polypeptide of an H3 subtype or an antigenic fragment thereof, wherein the sequence is at least 95% identical to SEQ ID NO:3, or comprises at least 30 contiguous nucleotides that are identical to 30 contiguous nucleotides of SEQ ID NO:3, and wherein the sequence is codon-optimized for expression in a mammalian cell; (b) a mammalian promoter operably linked to the nucleic acid molecule, wherein the promoter directs transcription of mRNA encoding the influenza polypeptide; and (c) a mammalian polyadenylation signal operably linked to the nucleic acid molecule, wherein the composition is administered in an amount sufficient for the sequence to express the influenza polypeptide at a level sufficient to induce an immune response in the subject.

11. The method of claim 10, further comprising administering to the subject a second composition comprising an influenza polypeptide.

12. The method of claim 10, wherein the second composition comprises influenza virions.

13. The method of claim 10, wherein the sequence is SEQ ID NO: 3.

14. The method of claim 10, wherein the antigenic fragment comprises an external domain of the HA polypeptide.

15. The method of claim 10, wherein the antigenic fragment comprises an HA1 domain of the HA polypeptide.

16. The method of claim 10, wherein the antigenic fragment comprises an HA2 domain of the HA polypeptide.

17. The method of claim 10, wherein the composition further comprises a second nucleic acid molecule comprising a second sequence encoding an influenza type HA polypeptide of an H1 subtype or an antigenic fragment thereof, wherein the second sequence has been codon-optimized for expression in a mammalian cell.

18. The method of claim 17, wherein the second sequence is at least 95% identical to SEQ ID NO:1, or comprises at least 30 contiguous nucleotides that are identical to 30 contiguous nucleotides of SEQ ID NO:1.

* * * * *

UNITED STATES PATENT AND TRADEMARK OFFICE
CERTIFICATE OF CORRECTION

| | | |
|---|---|---|
| PATENT NO. | : 7,566,454 B2 | Page 1 of 1 |
| APPLICATION NO. | : 11/362617 | |
| DATED | : July 28, 2009 | |
| INVENTOR(S) | : Lu et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 127 days.

Delete the phrase "by 127 days" and insert -- by 281 days --

Signed and Sealed this

First Day of June, 2010

David J. Kappos
*Director of the United States Patent and Trademark Office*